(12) United States Patent
Medved et al.

(10) Patent No.: US 8,722,623 B2
(45) Date of Patent: May 13, 2014

(54) COMPOSITIONS AND METHODS UTILIZING FIBRIN BETA CHAIN FRAGMENTS

(75) Inventors: Leonid Medved, Ellicott City, MD (US); Li Zhang, Boyds, MD (US); Sergiy Yakovlev, Rockville, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 587 days.

(21) Appl. No.: 12/678,122

(22) PCT Filed: Sep. 17, 2008

(86) PCT No.: PCT/US2008/010832
§ 371 (c)(1),
(2), (4) Date: Mar. 12, 2010

(87) PCT Pub. No.: WO2009/038729
PCT Pub. Date: Mar. 26, 2009

(65) Prior Publication Data
US 2012/0289467 A1 Nov. 15, 2012

Related U.S. Application Data

(60) Provisional application No. 60/972,986, filed on Sep. 17, 2007.

(51) Int. Cl.
*A61K 38/36* (2006.01)
*A61P 7/04* (2006.01)
*C07K 14/75* (2006.01)
*C07K 14/475* (2006.01)

(52) U.S. Cl.
USPC .................................................. 514/13.6

(58) Field of Classification Search
CPC ................................ A61K 38/00; C07K 14/75
See application file for complete search history.

(56) References Cited

U.S. PATENT DOCUMENTS

| 7,271,144 | B2 | 9/2007 | Petzelbauer |
| 2006/0263360 | A1 | 11/2006 | Goldstein |
| 2007/0048383 | A1* | 3/2007 | Helmus ........................ 424/489 |
| 2008/0004220 | A1* | 1/2008 | Petzelbauer et al. ............ 514/12 |

FOREIGN PATENT DOCUMENTS

| WO | WO 2007095659 A1 * | 8/2007 |
| WO | WO 2007095660 A1 * | 8/2007 |

OTHER PUBLICATIONS

Masson-Bessie' re rt al., The Journal of Immunology, 2001, 166: 4177-4184.*
Schlesinger et al., Cellular and Molecular Life Sci, 1977, 33 (3): 324-325.*
Zheng, Photocrosslinked Peg Hydrogel and Peptide Fluorescent Sensors for Copper Ions, Dissertation, University of Miami, 2002.*
Gorlatov et al., Biochemistry, 2002, 41, 4107-4116.*
Roberts et al., Advanced Drug Delivery Reviews, 2002, 54, 459-476.*
Jones, et al., British Journal of Pharmacology, 2005, 145, 1093-1102.*
Wadia et al., Current Opinion in Biotechnology 2002, 13:52-56.*
Petzelbauer et al., The fibrin-derived peptide Bβ15-42 protects the myocardium against ischemia-reperfusion injury, Nature Medicine, 11:298-304 (2005).
Roesner et al., The fibrin-derived peptide Bβ15-42 is cardioprotective in a pig model of myocardial ischemia-reperfusion injury, Crit Care Med, 35:1730-1735 (Jul. 2007).
Zacharowski et al., The Effects of the Fibrin-Derived Peptide Bβ15-42 in Acute and Chronic Rodent Models of Myocardial Ischemia-Reperfusion, SHOCK, 27:631-637 (Jun. 2007).

* cited by examiner

*Primary Examiner* — Marcela M Cordero Garcia
*Assistant Examiner* — Kaipeen Yang
(74) *Attorney, Agent, or Firm* — Nevrivy Patent Law Group P.L.L.C.

(57) ABSTRACT

A composition including a peptide sequence of the formula βX1-X2, the peptide sequence corresponding to an amino acid sequence of a fibrin beta chain fragment of a Bbeta chain of fibrinogen, wherein X1 represents an N-terminal end of the peptide sequence, and X2 represents a C-terminal end of the peptide sequence, wherein the peptide sequence includes additional amino acids between X1 and X2, wherein the peptide sequence may contain a non-naturally occurring amino acid residue, wherein the peptide sequence is other than a wild-type β15-42 monomer sequence per se, and wherein the peptide sequence is other than (β15-66)$_2$ dimer having two chains with each chain limited to wild type amino acids β15-65 and each chain further including a non-naturally occurring Gly at position 66 of each chain. Methods for treatment and pharmaceutical combinations may include a polypeptide agent such as Thymosin beta 4. In such methods and combinations, a dimer of the peptide sequence may include amino acids 15-66 of the fibrin beta chain.

17 Claims, 6 Drawing Sheets

*fibrinopeptide B* ↓
QGVNDNEEGFFSARGHRPLDKKREEAPSLRPAPPPISGGGYRARPAKAAATQKKVERKAPDAGGCG
1         10        20        30        40        50        60    *
FIG. 1A
$K_d$ = 252 μM   15  42
FIG. 1B
$K_d$ = 27 nM   15  ss 66
FIG. 1C
$K_d$ = 21 nM   15  ss 44
FIG. 1D

SEQUENCE LISTING

<160> NUMBER OF SEQ ID NOS: 20

<210> SEQ ID NO 1
<211> LENGTH: 1473
<212> TYPE: DNA
<213> ORGANISM: Homo sapiens

<400> SEQUENCE: 1

```
atgaaaagga tggtttcttg gagcttccac aaacttaaaa ccatgaaaca tctattattg      60
ctactattgt gtgtttttct agttaagtcc caaggtgtca acgacaatga ggagggtttc     120
ttcagtgccc gtggtcatcg accccttgac aagaagagag aagaggctcc cagcctgagg     180
cctgccccac cgcccatcag tggaggtggc tatcgggctc gtccagccaa agcagctgcc     240
actcaaaaga agtagaaaag aaaagcccct gatgctggag gctgtcttca cgctgaccca     300
gacctggggg tgttgtgtcc tacaggatgt cagttgcaag aggctttgct acaacaggaa     360
aggccaatca gaaatagtgt tgatgagtta ataacaatg tggaagctgt tcccagacc      420
tcctcttctt cctttcagta catgtatttg ctgaaagacc tgtggcaaaa gaggcagaag     480
caagtaaaag ataatgaaaa tgtagtcaat gagtactcct cagaactgga aaagcaccaa     540
ttatatatag atgagactgt gaatagcaat atcccaacta accttcgtgt gcttcgttca     600
atcctggaaa acctgagaag caaaatacaa agttagaat ctgatgtctc agctcaaatg      660
gaatattgtc gcaccccatg cactgtcagt tgcaatattc ctgtggtgtc tggcaaagaa     720
tgtgaggaaa ttatcaggaa aggaggtgaa acatctgaaa tgtatctcat tcaacctgac     780
agttctgtca aaccgtatag agtatactgt gacatgaata cagaaaatgg aggatggaca     840
gtgattcaga accgtcaaga cggtagtgtt gactttggca ggaaatggga tccatataaa     900
cagggatttg gaaatgttgc aaccaacaca gatgggaaga attactgtgg cctaccaggt     960
gaatattggc ttggaaatga taaaattagc cagcttacca ggatgggacc cacagaactt    1020
ttgatagaaa tggaggactg gaaaggagac aaagtaaagg ctcactatgg aggattcact    1080
gtacagaatg aagccaacaa ataccagatc tcagtgaaca atacagagg aacagccggt    1140
aatgccctca tggatggagc atctcagctg atgggagaaa acaggaccat gaccattcac    1200
aacggcatgt tcttcagcac gtatgacaga gacaatgacg gctggttaac atcagatccc    1260
agaaaacagt gttctaaaga agacggtggt ggatggtggt ataatagatg tcatgcagcc    1320
aatccaaacg gcagatacta ctggggtgga cagtacacct gggacatggc aaagcatggc    1380
acagatgatg gtgtagtatg gatgaattgg aagggtcat ggtactcaat gaggaagatg     1440
agtatgaaga tcaggccctt cttcccacag caa                                  1473
```

<210> SEQ ID NO 2
<211> LENGTH: 153
<212> TYPE: DNA
<213> ORGANISM: Artificial Sequence
<220> FEATURE:
<223> OTHER INFORMATION: Nucleic acid endocing fibrin beta chain derived
      fragment of a Bbeta chain of fibrinogen

<400> SEQUENCE: 2

```
ggtcatcgac cccttgacaa gaagagagaa gaggctccca gcctgaggcc tgccccaccg      60
cccatcagtg gaggtggcta tcgggctcgt ccagccaaag cagctgccac tcaaaagaaa     120
gtagaaagaa aagcccctga tgctggaggc tgt                                   153
```

-continued

```
<210> SEQ ID NO 3
<211> LENGTH: 51
<212> TYPE: PRT
<213> ORGANISM: Artificial Sequence
<220> FEATURE:
<223> OTHER INFORMATION: Fibrin beta chain derived fragment of a Bbeta
      chain of fibrinogen

<400> SEQUENCE: 3

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Ala Arg Pro Ala
            20                  25                  30

Lys Ala Ala Ala Thr Gln Lys Lys Val Glu Arg Lys Ala Pro Asp Ala
        35                  40                  45

Gly Gly Cys
    50

<210> SEQ ID NO 4
<211> LENGTH: 52
<212> TYPE: PRT
<213> ORGANISM: Artificial Sequence
<220> FEATURE:
<223> OTHER INFORMATION: Fibrin beta chain derived fragment of a Bbeta
      chain of fibrinogen

<400> SEQUENCE: 4

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Ala Arg Pro Ala
            20                  25                  30

Lys Ala Ala Ala Thr Gln Lys Lys Val Glu Arg Lys Ala Pro Asp Ala
        35                  40                  45

Gly Gly Cys Gly
    50

<210> SEQ ID NO 5
<211> LENGTH: 30
<212> TYPE: PRT
<213> ORGANISM: Artificial Sequence
<220> FEATURE:
<223> OTHER INFORMATION: Fibrin beta chain derived fragment of a Bbeta
      chain of fibrinogen

<400> SEQUENCE: 5

Gly His Arg Pro Leu Asp Lys Lys Arg Glu Glu Ala Pro Ser Leu Arg
1               5                   10                  15

Pro Ala Pro Pro Pro Ile Ser Gly Gly Gly Tyr Arg Cys Gly
            20                  25                  30

<210> SEQ ID NO 6
<211> LENGTH: 26
<212> TYPE: PRT
<213> ORGANISM: Artificial Sequence
<220> FEATURE:
<223> OTHER INFORMATION: Fibrin beta chain derived fragment of a Bbeta
      chain of fibrinogen

<400> SEQUENCE: 6

Gly His Arg Pro Leu Asp Lys Lys Arg Glu Glu Ala Pro Ser Leu Arg
1               5                   10                  15

Pro Ala Pro Pro Pro Ile Ser Tyr Cys Gly
            20                  25
```

```
<210> SEQ ID NO 7
<211> LENGTH: 21
<212> TYPE: PRT
<213> ORGANISM: Artificial Sequence
<220> FEATURE:
<223> OTHER INFORMATION: Fibrin beta chain derived fragment of a Bbeta
      chain of fibrinogen

<400> SEQUENCE: 7

Gly His Arg Pro Leu Asp Lys Lys Arg Glu Glu Ala Pro Ser Leu Arg
1               5                   10                  15

Pro Ala Tyr Cys Gly
            20

<210> SEQ ID NO 8
<211> LENGTH: 19
<212> TYPE: PRT
<213> ORGANISM: Artificial Sequence
<220> FEATURE:
<223> OTHER INFORMATION: Fibrin beta chain derived fragment of a Bbeta
      chain of fibrinogen

<400> SEQUENCE: 8

Gly His Arg Pro Leu Asp Lys Lys Arg Glu Glu Ala Pro Ser Leu Arg
1               5                   10                  15

Tyr Cys Gly

<210> SEQ ID NO 9
<211> LENGTH: 18
<212> TYPE: PRT
<213> ORGANISM: Artificial Sequence
<220> FEATURE:
<223> OTHER INFORMATION: Fibrin beta chain derived fragment of a Bbeta
      chain of fibrinogen

<400> SEQUENCE: 9

Gly His Arg Pro Leu Asp Lys Lys Arg Glu Glu Ala Pro Ser Leu Arg
1               5                   10                  15

Cys Gly

<210> SEQ ID NO 10
<211> LENGTH: 156
<212> TYPE: DNA
<213> ORGANISM: Artificial Sequence
<220> FEATURE:
<223> OTHER INFORMATION: Nucleic acid encoding fibrin beta chain derived
      fragment of a Bbeta chain of fibrinogen

<400> SEQUENCE: 10
ggtcatcgac cccttgacaa gaagagagaa gaggctccca gcctgaggcc tgccccaccg      60
cccatcagtg gaggtggcta tcgggctcgt ccagccaaag cagctgccac tcaaaagaaa     120
gtagaaagaa aagcccctga tgctggaggc tgtggc                               156

<210> SEQ ID NO 11
<211> LENGTH: 90
<212> TYPE: DNA
<213> ORGANISM: Artificial Sequence
<220> FEATURE:
<223> OTHER INFORMATION: Nucleic acid encoding fibrin beta chain derived
      fragment of a Bbeta chain of fibrinogen

<400> SEQUENCE: 11
ggtcatcgac cccttgacaa gaagagagaa gaggctccca gcctgaggcc tgccccaccg      60
cccatcagtg gaggtggcta tcggtgtggc                                       90
```

<210> SEQ ID NO 12
<211> LENGTH: 78
<212> TYPE: DNA
<213> ORGANISM: Artificial Sequence
<220> FEATURE:
<223> OTHER INFORMATION: Nucleic acid encoding fibrin beta chain derived fragment of a Bbeta chain of fibrinogen

<400> SEQUENCE: 12

```
ggtcatcgac cccttgacaa gaagagagaa gaggctccca gcctgaggcc tgccccaccg    60
cccatcagtt attgtggc                                                  78
```

<210> SEQ ID NO 13
<211> LENGTH: 63
<212> TYPE: DNA
<213> ORGANISM: Artificial Sequence
<220> FEATURE:
<223> OTHER INFORMATION: Nucleic acid encoding fibrin beta chain derived fragment of a Bbeta chain of fibrinogen

<400> SEQUENCE: 13

```
ggtcatcgac cccttgacaa gaagagagaa gaggctccca gcctgaggcc tgcctattgt    60
ggc                                                                  63
```

<210> SEQ ID NO 14
<211> LENGTH: 57
<212> TYPE: DNA
<213> ORGANISM: Artificial Sequence
<220> FEATURE:
<223> OTHER INFORMATION: Nucleic acid encoding fibrin beta chain derived fragment of a Bbeta chain of fibrinogen

<400> SEQUENCE: 14

```
ggtcatcgac cccttgacaa gaagagagaa gaggctccca gcctgaggta ttgtggc       57
```

<210> SEQ ID NO 15
<211> LENGTH: 54
<212> TYPE: DNA
<213> ORGANISM: Artificial Sequence
<220> FEATURE:
<223> OTHER INFORMATION: Nucleic acid encoding fibrin beta chain derived fragment of a Bbeta chain of fibrinogen

<400> SEQUENCE: 15

```
ggtcatcgac cccttgacaa gaagagagaa gaggctccca gcctgaggtg tggc          54
```

<210> SEQ ID NO 16
<211> LENGTH: 6
<212> TYPE: PRT
<213> ORGANISM: Artificial Sequence
<220> FEATURE:
<223> OTHER INFORMATION: Tbeta4 derived sequence

<400> SEQUENCE: 16

```
Leu Lys Lys Thr Glu Thr
1               5
```

<210> SEQ ID NO 17
<211> LENGTH: 6
<212> TYPE: PRT
<213> ORGANISM: Artificial Sequence

```
<220> FEATURE:
<223> OTHER INFORMATION: Tbeta4 derived sequence

<400> SEQUENCE: 17

Leu Lys Lys Thr Asn Thr
1               5

<210> SEQ ID NO 18
<211> LENGTH: 7
<212> TYPE: PRT
<213> ORGANISM: Artificial Sequence
<220> FEATURE:
<223> OTHER INFORMATION: Tbeta4 derived sequence

<400> SEQUENCE: 18

Lys Leu Lys Lys Thr Glu Thr
1               5

<210> SEQ ID NO 19
<211> LENGTH: 7
<212> TYPE: PRT
<213> ORGANISM: Artificial Sequence
<220> FEATURE:
<223> OTHER INFORMATION: Tbeta4 derived sequence

<400> SEQUENCE: 19

Leu Lys Lys Thr Glu Thr Gln
1               5

<210> SEQ ID NO 20
<211> LENGTH: 66
<212> TYPE: PRT
<213> ORGANISM: Homo sapiens

<400> SEQUENCE: 20

Gln Gly Val Asn Asp Asn Glu Glu Gly Phe Phe Ser Ala Arg Gly His
1               5                   10                  15

Arg Pro Leu Asp Lys Lys Arg Glu Glu Ala Pro Ser Leu Arg Pro Ala
                20                  25                  30

Pro Pro Pro Ile Ser Gly Gly Gly Tyr Arg Ala Arg Pro Ala Lys Ala
            35                  40                  45

Ala Ala Thr Gln Lys Lys Val Glu Arg Lys Ala Pro Asp Ala Gly Gly
        50                  55                  60

Cys Gly
65
```

COMPOSITIONS AND METHODS UTILIZING FIBRIN BETA CHAIN FRAGMENTS

CROSS REFERENCE TO RELATED APPLICATION

This application is the U.S. National Stage Application under 35 U.S.C. §371 of International Application No. PCT/US2008/010832, with an international filing date of Sep. 17, 2008, which claims the benefit under 35 U.S.C. §119 (e) of U.S. Provisional Application No. 60/972,986, filed Sep. 17, 2007.

REFERENCE TO A SEQUENCE LISTING SUBMITTED ELECTRONICALLY VIA EFS-WEB

The content of the sequence listing (Name: Seq_listing_ST25.txt, Size: 9,117 bytes; and Date of Creation: Jun. 11, 2012) electronically submitted via EFS-Web is incorporated by reference in its entirety.

BACKGROUND OF THE INVENTION

1. Field of the Invention

The present invention relates to the field of compositions and methods utilizing fibrin beta chain fragments of the Bbeta chain of fibrinogen.

2. Description of the Background Art

Localized leukocyte accumulation is the cellular hallmark of inflammation. Although this has been recognized for more than a century, it is only in the past decade that the role of the endothelium has been appreciated. The notion that the vascular endothelium actively participates in leukocyte recruitment initially gained support from in vitro studies demonstrating that treatment of cultured endothelium with certain inflammatory cytokines activate the endothelium to become adhesive for blood leukocytes and cell lines.

Reperfusion injury refers to damage to tissue (e.g., heart tissue) caused when blood supply returns to the tissue after a period of ischemia. The absence of oxygen and nutrients from blood creates a condition in which the restoration of circulation results in inflammation and other damage.

The damage of reperfusion injury is due in part to the inflammatory response of damaged tissues. White blood cells (leukocytes) carried to the area by the newly returning blood release a host of inflammatory factors such as interleukins as well as free radicals in response to tissue damage.

There remains a need in the art for methods of inhibiting inflammation and treating ischemia and reperfusion.

SUMMARY OF THE INVENTION

In accordance with one aspect of the present invention, methods and compositions utilize a composition comprising, consisting essentially of, or consisting of a peptide sequence of the formula $\beta X1-X2$, said peptide sequence corresponding in whole or in part to an amino acid sequence of a fibrin beta chain fragment of a Bbeta chain of fibrinogen, wherein X1 represents an N-terminal end of said peptide sequence and X2 represents a C-terminal end of said peptide sequence, wherein said peptide sequence includes additional amino acids between X1 and X2, wherein said peptide sequence may contain a non-naturally occurring amino acid residue, wherein said peptide sequence is other than a wild-type $\beta$15-42 monomer sequence per se, and wherein said peptide sequence is other than $(\beta 15-66)_2$ dimer having two chains with each chain consisting of wild type amino acids $\beta$15-65 and with each chain including a non-naturally occurring Gly at position 66 of each chain. In certain embodiments, the methods and compositions utilize a monomer or dimer of the peptide sequence in combination with a polypeptide agent comprising or consisting essentially of at least one of thymosin $\beta$4 (TB4 or T$\beta$4), an N-terminal variant of TB4, a C-terminal variant of TB4, LKKTET (SEQ ID NO:16) or a conservative variant thereof, LKKTNT (SEQ ID NO:17) or a conservative variant thereof, KLKKTET (SEQ ID NO:18) or a conservative variant thereof, LKKTETQ (SEQ ID NO:19) or a conservative variant thereof, TB4 sulfoxide, T$\beta 4^{ala}$, T$\beta$9, T$\beta$10, T$\beta$11, T$\beta$12, T$\beta$13, T$\beta$14, T$\beta$15, gelsolin, vitamin D binding protein (DBP), profilin, cofilin, adsevertin, propomyosin, fincilin, depactin, DnaseI, vilin, fragmin, severin, capping protein, $\beta$-actinin, acumentin or conservative variants of any of the above.

BRIEF DESCRIPTION OF THE DRAWINGS

FIG. 1a shows the amino acid sequence of fibrinopeptide B (SEQ ID NO:20).

FIG. 1b is a schematic representation of a monomeric $\beta$15-42 fragment of the sequence shown in FIG. 1a.

FIG. 1c is a schematic representation of a dimeric $(\beta 15-66)_2$ peptide.

FIG. 1d schematically represents a $(\beta 15-44)_2$ peptide.

DETAILED DESCRIPTION OF THE INVENTION

Definitions

Figure 2:
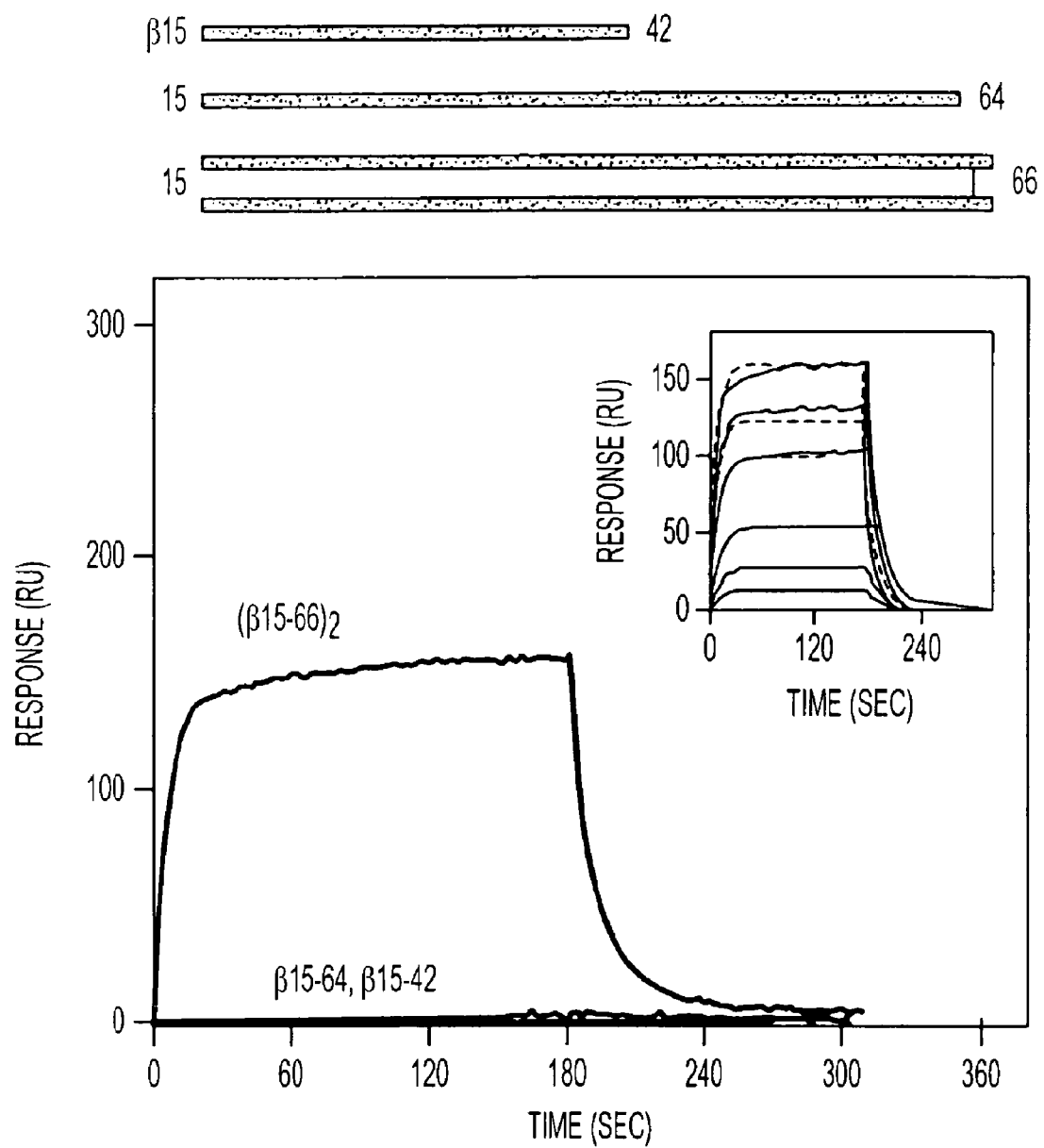
FIG. 2 graphically demonstrates binding of ($\beta$15-66)2, $\beta$15-64, and $\beta$15-42 to VE-cadherin.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein in the claim(s), when used in conjunction with the word "comprising", the words "a" or "an" may mean one or more than one. As used herein "another" may mean at least a second or more. Furthermore, unless otherwise required by context, singular terms include pluralities and plural terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

As used herein, a "fibrin beta chain derived peptide," a "peptide derivative of fibrin beta chain" or an obvious modification hereof means a peptide derived from the Bbeta chain of fibrinogen (see, for example, Petzelbauer et al. Nat Med. 2005 March; 11(3):298-304. Epub 2005 Feb. 20; Gorlatov et al. Biochemistry (2002) 41, 4107-4116; U.S. Pat. No. 4,980,456; GENE BANK ACCESSION NO. NP_005132). Such peptides can be in the form of a monomer or dimer. If the peptide is not indicated to be in the monomeric or dimeric form, the peptide encompasses both the monomeric and dimeric form.

As used herein, a "therapeutically effective amount" or a "therapeutic effective amount" is an amount of a peptide and/or compound and a composition comprising the same of the invention (including, for example, a fibrin beta chain derived peptide or a combination of the same with TB4 or an isoform, analogue, or derivative of TB4) that alleviates, totally or partially, the pathophysiological effects of inflammation, myocardial ischemia and reperfusion, or other pathological indication of the invention. Unless otherwise indicated when referring to the administration of any peptide and/or compound and a composition comprising the same of the invention, said peptide and/or compound and a composition comprising the same is administered at a concentration that is a therapeutically effective amount or a therapeutic effective amount. A therapeutically effective amount or a therapeutic effective amount can also be an amount that is given prophylactically thereby inhibiting any pathophysiological effects of inflammation, myocardial ischemia and reperfusion, or other pathological indication of the invention. A therapeutically effective amount or a therapeutic effective amount will depend upon, for example, subject size, gender, magnitude of the associated disease, condition, or injury, and genetic or non-genetic factors associated with individual pharmacokinetic or pharmacodynamic properties of the administered peptide and/or compound or a composition comprising the same. For a given subject in need thereof a therapeutically effective amount or a therapeutic effective amount can be determined by one of ordinary skill in the art and by methods known to one of ordinary skill in the art.

As used herein, "treat" and all its forms and tenses (including, for example, treat, treating, treated, and treatment) refer to both therapeutic treatment and prophylactic or preventative treatment. A subject in need thereof of treatment include those already with a pathological condition of the invention as well as those in which a pathological condition of the invention is to be prevented.

In accordance with one embodiment, inflammation in a subject is inhibited by administration to the subject of a synthetic peptide dimer composition comprising two peptide sequences, each of said sequences comprising amino acids 15-42 of a fibrin beta chain or a VE-cadherin-binding conservative variant thereof, each of said sequences being linked at C-terminal ends thereof, said dimer having fewer than 104 amino acid residues in total. In another embodiment, the fibrin beta chain or a VE-cadherin-binding conservative variant thereof comprises amino acids 15-32.

It was shown by Petzelbauer et al. (Nature Medicine, 11:3, 298-304, March 2005) that the interaction of fibrin with the endothelial cell receptor VE-cadherin supports transendothelial migration of leukocytes thereby promoting inflammation. They also demonstrated that a β15-42 peptide, which includes amino acid residues 15-42 of the fibrin β chain, competes with fibrin for the interaction with VE-cadherin thereby inhibiting this interaction. Furthermore, the same study demonstrated that in acute or chronic rat models of myocardial ischemia-reperfusion injury the β15-42 peptide, by inhibiting leukocyte transmigration, substantially reduced myocardial inflammation and infarct size. This peptide was proposed to be a potential drug candidate for reperfusion therapy in humans (Zacharowski et al., J. Mol. Med., 84:469-477, 2006).

Although the β15-42 peptide interacts with VE-cadherin, we found that its affinity to the latter is weak. Our analysis of the fibrinogen structure suggested that the β15-42 region represents only a portion of the fibrin βN-domain, which includes the β chain residues 15-64 (Gorlatov and Medved, Biochemistry, 41:4107-4116, 2002). To test if the complete 13N-domain is functionally superior over the 1315-42 peptide, we prepared a recombinant dimeric version of this domain, (β15-66)$_2$, in which two β15-66 peptides were disulfide-linked via Cys65 to mimic the dimeric arrangement of these domains in fibrin, and confirmed that such a dimer has much higher affinity to VE-cadherin than β15-42 (Gorlatov and Medved, supra).

FIG. 1a shows the amino acid sequence of the fibrinogen (B) β N-domain. FIG. 1b is a schematic representation of the monomeric β15-42. FIG. 1c is a dimeric (β15-66)$_2$, and FIG. 1d is a dimeric (β15-44)$_2$ peptide. The dissociation constants (affinities) for the interaction of the peptides with VE-cadherin are indicated at the left in FIGS. 1a-1d.

In certain embodiments, the invention is directed to a pharmaceutical combination comprising a dimer as disclosed herein, and a polypeptide agent comprising or consisting essentially of at least one of thymosin β4 (TB4), an isoform of TB4, an N-terminal variant of TB4, a C-terminal variant of TB4, LKKTET (SEQ ID NO:16) or a conservative variant thereof, LKKTNT (SEQ ID NO:17) or a conservative variant thereof, KLKKTET (SEQ ID NO:18) or a conservative variant thereof, LKKTETQ (SEQ ID NO:19) or a conservative variant thereof, TB4 sulfoxide, Tβ4$^{ala}$, Tβ9, Tβ10, Tβ11, Tβ12, Tβ13, Tβ14, Tβ15, gelsolin, vitamin D binding protein (DBP), profilin, cofilin, adsevertin, propomyosin, fincilin, depactin, DnaseI, vilin, fragmin, severin, capping protein, β-actinin, acumentin or conservative variants of any of the above.

Thymosin β4 (Tβ4) is a member of the β-thymosin family of highly conserved 4.9-kDa polypeptides found in various tissues and cell types. Originally purified from the thymus and regarded as a thymic hormone, Tβ4 was then found to be involved in multiple biological processes. As the main G-actin sequestering peptide, it plays an important role in regulation of actin assembly during cell proliferation, migration, and differentiation. Numerous studies implicate Tβ4 in the regulation of angiogenesis, inflammation, and wound healing. It was found that Tβ4 is expressed in specific cardiac cell types during development and promotes cardiac cell migration and survival. Furthermore, it was shown using a mouse model that Tβ4 promotes survival of cardiomyocytes and cardiac repair after coronary artery ligation. The cardioprotective effect of Tβ4 has been confirmed in a recent study, which identified Tβ4 as a potent stimulator of coronary vasculogenesis and angiogenesis, and revealed a mechanism by which Tβ4 may act to promote cardiomyocyte survival following acute myocardial damage in mice.

As noted above, the invention includes synthetic peptide dimer compositions comprising two peptide sequences, each of the sequences comprising amino acids 15-42 of a fibrin beta chain, each of the sequences being linked at C-terminal ends thereof. In certain embodiments, the dimer has fewer than 104 amino acid residues in total. In certain embodiments, the dimer may further comprise at least one additional amino acid residue, or more than one additional amino acid residues. For example, each peptide chain of the dimer may include additional amino acid residues between amino acids 42 and 66 of the fibrin beta chain. For example, the invention may utilize the (β15-66)$_2$ dimer shown in FIG. 1c, or conservative variants thereof.

In certain embodiments, the dimer comprises the (β15-44)$_2$ dimer shown in FIG. 1d, or conservative variants thereof.

In accordance with one embodiment of the present invention, a pharmaceutical combination is provided comprising a dimer as described herein, and a polypeptide agent as described herein, which can be administered separately or together.

In accordance with one embodiment, a method is provided for inhibiting inflammation of tissue of a subject, comprising administering the subject a peptide dimer as described herein having fewer than 104 amino acid residues in total, or administering a peptide dimer which further comprises at least one additional amino acid residue. Non-limiting examples include the (β15-44)$_2$ dimer and the (β15-66)$_2$ dimer. In particular embodiments, the tissue is muscle tissue, particularly cardiac tissue.

Certain embodiments include a pharmaceutical combination comprising a dimer as described herein having at least one additional amino acid residue (e.g., having 104 or more amino acid residues in total), and a polypeptide agent as described herein, wherein the dimer and the polypeptide agent may be administered separately or together. An exemplary dimer for utilization in this embodiment is the (β15-66)$_2$ dimer.

In certain particular embodiments, the dimer has 60 amino acid residues in total, e.g., the (β15-44)$_2$ dimer. There are 30 amino acid residues in each of two polypeptide chains of the (β15-44)$_2$ peptide; the first 28 residues of each chain correspond to the natural β15-42 sequence of human fibrin, while the last two residues, Cys43 and Gly44, were added to link two polypeptide chains together through a Cys43-Cys43 disulfide bond.

In other particular embodiments, the dimer has 104 amino acid residues in total, e.g., the (β15-66)$_2$ dimer. There are 52 amino acid residues in each of two polypeptide chains of the (β15-66)$_2$ peptide; the first 51 residues including Cys65 of each chain correspond to the natural β15-65 sequence of human fibrin, while the last residue, Gly66, was added to facilitate formation of a Cys65-Cys66 disulfide bond.

The invention may also include dimers including one or more naturally occurring or substituted amino acid residues between residues 42 and 66 of the fibrin beta chain. The two peptide sequences of the dimer may be the same length, or different lengths. One or more amino acids may be substituted for the naturally occurring amino acids of the fibrin beta chain, so long as the dimer retains VE-cadherin binding affinity.

The dimers disclosed herein can be manufactured using solid phase peptide synthesis or recombinant manufacturing methods known in the art.

In accordance with one aspect, a method of treatment for inhibiting inflammation and tissue protection and/or regeneration in tissue of a subject, comprises administering to a subject in need of such treatment an effective amount of a dimer as disclosed herein and a composition comprising polypeptide agent comprising or consisting essentially of at least one of thymosin β4 (TB4), an isoform of TB4, an N-terminal variant of TB4, a C-terminal variant of TB4, LKKTET (SEQ ID NO:16) or a conservative variant thereof, LKKTNT (SEQ ID NO:17) or a conservative variant thereof, KLKKTET (SEQ ID NO:18) or a conservative variant thereof, LKKTETQ (SEQ ID NO:19) or a conservative variant thereof, TB4 sulfoxide, Tβ4$^{ala}$, Tβ9, Tβ10, Tβ11, Tβ12, Tβ13, Tβ14, Tβ15, gelsolin, vitamin D binding protein (DBP), profilin, cofilin, adsevertin, propomyosin, fincilin, depactin, DnaseI, vilin, fragmin, severin, capping protein, β-actinin or acumentin, in said tissue, so as to inhibit said microbial infection.

Polypeptide agents such as thymosin β4 (Tβ4 or TB4) and other actin-sequestering peptides or peptide fragments, some of which may contain amino acid sequence LKKTET (SEQ ID NO:16), LKKTNT (SEQ ID NO:17), or conservative variants thereof, promote tissue protection and/or regeneration.

A subject being treated in accordance with the present invention preferably is mammalian, most preferably human.

Thymosin 4 was initially identified as a protein that is up-regulated during endothelial cell migration and differentiation in vitro. Thymosin 4 was originally isolated from the thymus and is a 43 amino acid, 4.9 kDa ubiquitous polypeptide identified in a variety of tissues. Several roles have been ascribed to this protein including a role in a endothelial cell differentiation and migration, T cell differentiation, actin sequestration, vascularization and wound healing.

In accordance with one embodiment, the invention is a method of inhibiting inflammation and tissue protection and/or regeneration, comprising administering to a subject an effective amount of a dimer as disclosed herein and a composition comprising a polypeptide agent, which may be a polypeptide comprising or consisting essentially of at least one of thymosin β4 (TB4), an isoform of TB4, an N-terminal variant of TB4, a C-terminal variant of TB4, LKKTET (SEQ ID NO:16) or a conservative variant thereof, LKKTNT (SEQ ID NO:17) or a conservative variant thereof, KLKKTET (SEQ ID NO:18) or a conservative variant thereof, LKKTETQ (SEQ ID NO:19) or a conservative variant thereof, TB4 sulfoxide, Tβ4$^{ala}$, Tβ9, Tβ10, Tβ11, Tβ12, Tβ13, Tβ14b, Tβ15, gelsolin, vitamin D binding protein (DBP), profilin, cofilin, adsevertin, propomyosin, fincilin, depactin, DnaseI, vilin, fragmin, severin, capping protein, β-actinin or acumentin. In accordance with other embodiments, the agent is other than thymosin beta 4 or Tβ4 sulfoxide.

International Application Serial No. PCT/US99/17282, incorporated herein by reference, discloses isoforms of Tβ4 which may be useful in accordance with the present invention as well as amino acid sequence LKKTET (SEQ ID NO:16) and conservative variants thereof, which may be utilized with the present invention. International Application Serial No. PCT/GB99/00833 (WO 99/49883), incorporated herein by reference, discloses oxidized Thymosin β4 which may be utilized in accordance with the present invention. Although the present invention is described primarily hereinafter with respect to T β4 and T β4 isoforms, it is to be understood that the invention is intended to be equally applicable to amino acid sequences LKKTET (SEQ ID NO:16), LKKTNT (SEQ ID NO:17), KLKKTET (SEQ ID NO:18) or LKKTETQ (SEQ ID NO:19), peptides and fragments comprising or consisting essentially of LKKTET (SEQ ID NO:16), LKKTNT (SEQ ID NO:17), KLKKTET (SEQ ID NO:18) or LKKTETQ (SEQ ID NO:19), conservative variants thereof having antimicrobial activity, and/or Tβ4 isoforms, analogues or derivatives, including N-terminal variants of Tβ4, C-terminal variants of Tβ4, Tβ4$^{ala}$, Tβ9, Tβ10, Tβ11, Tβ12, Tβ13, Tβ14, Tβ15, gelsolin, vitamin D binding protein (DBP), profilin, cofilin, adsevertin, propomyosin, fincilin, depactin, DnaseI, vilin, fragmin, severin, capping protein, β-actinin or acumentin.

In one embodiment, the invention provides a method of treatment for treating, inhibiting, reducing or at least partly preventing inflammation in a subject, and promoting tissue protection and/or regeneration by contacting the tissue with an effective amount of a composition or compositions which contain a dimer as disclosed herein and an agent as described herein. As non-limiting examples, the tissue may be selected from coronary tissue of said subject. In one embodiment, the invention provides a method for treating or reducing reperfusion injury caused by myocardial infarction in a subject by contacting an area to be treated with an effective amount of a composition or compositions as described herein. The contacting may be directly or systemically. Examples of direct administration include, for example for heart tissue, by injecting solution(s) of the inventive composition(s) directly into the tissue. Systemic administration includes, for example, intravenous, intraperitoneal, intramuscular injections or infusions of composition(s) as described herein, in pharmaceutically acceptable carrier(s) such as water for injection. Systemic administration may also include, for example, intramuscular or subcutaneous injections, or inhalation, transdermal or oral administration.

Dimers and polypeptide agents for use in the invention, as described herein, may be administered in any effective amount. For example, dimer(s) and polypeptide agent(s) as described herein may be administered in dosages of each within the range of about 0.0001-1,000,000 micrograms, in amounts within the range of about 0.1-5,000 micrograms, and in amounts within the range of about 1-30 micrograms. Such dosages may be measured in a ug/kg or mg/kg basis. The concentrations of the $(15-66)_2$ and $(15-44)_2$ peptides that were used to test the anti-inflammatory effects in a mouse model were 8.6 and 5.1 mg/kg, respectively. Based on much higher affinity of these peptides to VE-cadherin than that of β15-42 monomer it is believed that the same effect can be achieved at lower (e.g., 10-1000-fold) concentrations.

Composition(s) in accordance with the present invention can be administered daily, every other day, every other week, every other month, etc., with a single application or multiple applications per day of administration, such as applications 2, 3, 4 or more times per day of administration.

Many Tβ4 isoforms have been identified and have about 70%, or about 75%, or about 80% or more homology to the known amino acid sequence of Tβ4. Such isoforms include, for example, Tβ4$^{ala}$, Tβ9, Tβ10, Tβ11, Tβ12, Tβ13, Tβ14 and Tβ15. Similar to Tβ4, the Tβ10 and Tβ15 isoforms have been shown to sequester actin. Tβ4, Tβ10 and Tβ15, as well as these other isoforms share an amino acid sequence, LKKTET (SEQ ID NO:16) or LKKTNT (SEQ ID NO:17), that appears to be involved in mediating actin sequestration or binding. For example, Tβ4 can modulate actin polymerization (e.g. β-thymosins appear to depolymerize F-actin by sequestering free G-actin). Tβ4's ability to modulate actin polymerization may therefore be due to all, or in part, its ability to bind to or sequester actin via the LKKTET (SEQ ID NO:16) sequence. Thus, as with Tβ4, other proteins which bind or sequester actin, or modulate actin polymerization, including Tβ4 isoforms having the amino acid sequence LKKTET (SEQ ID NO:16), are likely to be effective, alone or in a combination with Tβ4, as set forth herein.

Thus, it is specifically contemplated that known Tβ4 isoforms, such as Tβ4$^{ala}$, Tβ9, Tβ10, Tβ11, Tβ12, Tβ13, Tβ14 and Tβ15, as well as Tβ4 isoforms not yet identified, will be useful in the methods of the invention. As such Tβ4 isoforms are useful in the methods of the invention, including the methods practiced in a subject. The invention therefore further provides pharmaceutical compositions comprising Tβ4, or conservative variants thereof, as well as Tβ4 isoforms Tβ4$^{ala}$, Tβ9, Tβ10, Tβ11, Tβ12, Tβ13, Tβ14, Tβ15 or conservative variants thereof, and a pharmaceutically acceptable carrier.

In addition, other agents or proteins having actin sequestering or binding capability, or that can mobilize actin or modulate actin polymerization, as demonstrated in an appropriate sequestering, binding, mobilization or polymerization assay, or identified by the presence of an amino acid sequence that mediates actin binding, such as LKKTET (SEQ ID NO:16) or LKKTNT (SEQ ID NO:17), for example, can similarly be employed in the methods of the invention. Such proteins may include gelsolin, vitamin D binding protein (DBP), profilin, cofilin, depactin, DnaseI, vilin, fragmin, severin, capping protein, β-actinin and acumentin, for example. As such methods include those practiced in a subject, the invention further provides pharmaceutical compositions comprising gelsolin, vitamin D binding protein (DBP), profilin, cofilin, depactin, DnaseI, vilin, fragmin, severin, capping protein, β-actinin and acumentin as set forth herein. The invention includes the use of a polypeptide agent comprising the amino acid sequence LKKTET (SEQ ID NO:16), LKKTNT (SEQ ID NO:17), KLKKTET (SEQ ID NO:18) or LKKTETQ (SEQ ID NO:19), and conservative variants thereof.

As used herein, the term "conservative variant" or grammatical variations thereof denotes the replacement of an amino acid residue by another, biologically similar residue. Examples of conservative variations include the replacement of a hydrophobic residue such as isoleucine, valine, leucine or methionine for another, the replacement of a polar residue for another, such as the substitution of arginine for lysine, glutamic for aspartic acids, or glutamine for asparagine, and the like.

Tβ4 has been localized to a number of tissue and cell types and thus, agents which stimulate the production of an LKKTET (SEQ ID NO:16) or LKKTNT (SEQ ID NO:17) peptide such as Tβ4 or another agent as described herein, can be added to or comprise a composition to effect production of an agent from a tissue and/or a cell. Such stimulating agents may include members of the family of growth factors, such as insulin-like growth factor (IGF-1), platelet derived growth factor (PDGF), epidermal growth factor (EGF), transforming growth factor beta (TGF-β), basic fibroblast growth factor (bFGF), thymosin α1 (Tα1) and vascular endothelial growth factor (VEGF). In particular embodiments, the stimulating agent is transforming growth factor beta (TGF-β) or other members of the TGF-β superfamily.

In accordance with one embodiment, subjects are treated with a stimulating agent that stimulates production in the subject of an agent as defined herein.

The invention also includes pharmaceutical composition(s) comprising a therapeutically effective amount(s) of dimer(s) and agent(s) as described herein in pharmaceutically acceptable carrier(s) such as water for injection.

The actual dosage or reagent, formulation or composition that provides treatment may depend on many factors, including the size and health of a subject. However, persons of ordinary skill in the art can use teachings describing the methods and techniques for determining clinical dosages as disclosed in PCT/US99/17282, supra, and the references cited therein, to determine the appropriate dosage to use.

Suitable formulations may include, for example, dimer(s) and agent(s) as described herein at concentration(s) of each within the range of about 0.001-50% by weight, within the range of about 0.01-0.1% by weight, and within the range of about 0.05% by weight.

The therapeutic approaches described herein involve various routes of administration or delivery of an agent as described herein, including any conventional administration techniques (for example, but not limited to, direct administration, local injection, inhalation, or systemic administration), to a subject. The methods and compositions using or containing dimer(s) and agent(s) as described herein may be formulated into pharmaceutical compositions by admixture with pharmaceutically acceptable non-toxic excipients or carriers.

In certain embodiments of the invention, the invention is drawn a novel fibrin beta chain derived peptide, compositions comprising the same, and methods of, for example, using or treating with the same. For example, peptides are truncated, engineered or modified, and/or dimerized. A fibrin beta chain derived peptide of the invention can be a sequence consisting of a particular noted or recited sequence or comprising a particular noted or recited sequence. Additionally compositions of a fibrin beta chain derived peptide can be a composition consisting of a particular noted or recited sequence, consisting essentially of a particular noted or recited sequence, or comprising a particular noted or recited sequence. In terms of administering a fibrin beta chain derived peptide or composition thereof with another peptide or composition thereof (including, for example, TB4 or an isoform, analogue, or derivative of TB4), the fibrin beta chain derived peptide or composition thereof can be administered prior to, concurrent with, or subsequent to the other peptide or composition thereof.

In other certain embodiments of the invention, the invention is drawn to an isolated nucleic acid sequence encoding a novel fibrin beta chain derived peptide. The scope of the nucleic acid sequences encompassed by the invention takes into consideration the degeneracy of the genetic code (i.e., that an amino acid may be translated from more than one codon). Therefore, nucleic acid sequences of the invention can differ from one another while still encoding the same amino acid sequence. A person of ordinary skill in the art can determine those sequences encompassed by the invention by no more than routine means by using the peptide sequences provided herein.

It is noted that the dimeric form of a fibrin beta chain derived peptide is represented, for example, using the following formula: (βX1-X2)2 wherein "X1" and "X2" indicate an amino position of the Bbeta chain of fibrinogen with or without any additional non-naturally occurring amino acid residues and "2" following the parenthesis indicates that the fibrin beta chain derived peptide exists as a dimer. In certain embodiments described herein, a fibrin beta chain derived peptide in dimeric form has an additional non-naturally occurring amino acid(s) at the C-terminus of the peptide. In other certain embodiments described herein, a fibrin beta chain derived peptide in dimeric form has an additional non-naturally occurring amino acid(s) at the N-terminus end of the peptide.

A fibrin beta chain derived peptide of the invention includes both the isolated monomeric form and dimeric form. Such sequences include, for example, those consisting of or comprising the isolated wild-type sequence β15-26, β15-27, β15-28, β15-29, β15-30, β15-31, β15-32, β15-33, β15-34, β15-35, β15-36, β15-37, β15-38, β15-39, β15-40, β15-41, β15-42, β15-43, β15-44, β15-45, β15-46, β15-47, β15-48, β15-49, β15-50, β15-51, β15-52, β15-53, β15-54, β15-55, β15-56, β15-57, β15-58, β15-59, β15-60, β15-61, β15-62, β15-63, β15-64, β15-65, β15-66, β15-67, β15-68, β15-69, β15-70, β15-71, β15-72, and β15-73. Homodimers of these peptides can be formed by, for example, modifying the isolated peptide by engineering a Cys (or a Gly in the case of, for example, β15-65) at the end of the sequence, a Cys and a Gly at the end of the sequence, a Tyr, a Cys, and a Gly at the end of the sequence, or other means for producing a homodimeric form of these peptides (see, for example, US Patent Application Publication Nos. 20070225221 20070142295, 20070093418, 20070049532, 20060122370, 20060002931, 20050152896, and 20020051785; U.S. Pat. Nos. 5,767,078 and 7,011,834). In particular embodiments (and for illustrative purposes), a dimer consisting of or comprising (β15-66)2 has a non-naturally occurring Gly at position 66 (i.e., amino acid 15-65 correspond to the native protein), (β15-44)2 has a non-naturally occurring Cys at position 43 and Gly at position 44 (i.e., amino acid 15-42 correspond to the native protein), (β15-40)2 has a non-naturally occurring Tyr at position 38, Cys at position 39, and Gly at position 40 (i.e., amino acid 15-37 correspond to the native protein), (β15-39)2 has a non-naturally occurring Cys at position 38, and Gly at position 39 (i.e., amino acid 15-37 correspond to the native protein), (β15-35)2 has a non-naturally occurring Tyr at position 33, Cys at position 34, and Gly at position 35 (i.e., amino acid 15-32 correspond to the native protein), (β15-34)2 has a non-naturally occurring Cys at position 33, and Gly at position 34 (i.e., amino acid 15-32 correspond to the native protein), (β15-33)2 has a non-naturally occurring Tyr at position 31, Cys at position 32, and Gly at position 33 (i.e., amino acid 15-30 correspond to the native protein), (β15-32)2 has a non-naturally occurring Cys at position 31, and Gly at position 32 (i.e., amino acid 15-30 correspond to the native protein), (β15-29)2 has a non-naturally occurring Tyr at position 27, Cys at position 28, and Gly at position 29 (i.e., amino acid 15-26 correspond to the native protein), (β15-28)2 has a non-naturally occurring Cys at position 27, and Gly at position 28 (i.e., amino acid 15-26 correspond to the native protein). In additional embodiments, the invention not only encompasses monomers described herein as homodimers, but also any combination of heterodimers. In even further additional embodiments, residues of the native sequence (including, for example, residues 18 and 20) can be mutated by replacing the wild-type amino acid with another natural or non-natural occurring amino acid (see, for example, U.S. Pat. No. 6,783,946). Naturally occurring amino acids include, for example, alanine (A), arginine (R), asparagine (N), aspartic acid (D), cysteine (C), glutamic acid (E), glutamine (Q), glycine (G), histidine (H), isoleucine (I), leucine (L), lysine (K), methionine (M), phenylalanine (F), proline (P), serine (S), threonine (T), tryptophan (W), tyrosine (Y), and valine (V). In certain embodiments, substitutions are conservative substitutions. In other embodiments, the substitutions are non-conservative substitutions. In particular embodiments, position 18 is mutated from a P to an A and/or position 20 is mutated from a D to an N (see, for example, Gorlatov et al. Biochemistry (20020 41, 4107-4116).

Conservative and non-conservative amino acid substitutions are known to those of ordinary skill in the art, for example, substituting an acidic amino acid for another acid amino acid may be considered a conservative substitution whereas substituting a basic amino acid for an acidic amino acid may be considered a non-conservative substitution; similarly, substituting a polar amino acid for another polar acid may be considered a conservative substitution whereas substituting a nonpolar amino acid for a polar amino acid may be considered a non-conservative substitution. Amino acids are generally grouped into the following categories (which can be used as a guide for determing whether or not a substitution is conservative or non-conservative): (1) polar/hydrophilic: N, Q, S, T, K, R, H, D, E, C, and Y; (2) non-polar/hydrophobic:

G, A, V, L, I, P, Y, F, W, M, and C; (3) acidic: D, E, and C; (4) basic: K, R, and H; (5) aromatic: F, W, Y, and H; and (6) aliphatic: G, A, V, L, I, and P.

In certain embodiments, the invention is drawn to a method of treatment. In particular embodiments, a method of treatment is directed to a mammal including for example, a dog, cat, monkey, goat, pig, orangutan, cow, horse, sheep, rabbit, guinea pig, rat, hamster, mouse, and human. In other particular embodiments, the invention is draw to treating a pathophysiological effect of inflammation, myocardial ischemia and reperfusion, or other pathological indication. In even further particular embodiments, the invention is draw to treating a pathophysiological effect of inflammation, myocardial ischemia and reperfusion, or other pathological indication wherein such is present as an acute condition as opposed to a long-term or chronic condition.

In certain embodiments of the invention drawn to myocardial infarction (commonly referred to as a heart attack or cardiac tissue damage as a result of hypoxia), stroke, and other types of organ or tissue ischemia and reperfusion (including, for example, hepatic ischemia and reperfusion, renal ischemia and reperfusion, intestinal ischemia and reperfusion, or other gastrointestinal ischemia and reperfusion, neuronal ischemia and reperfusion, ischemic neuropathies, surgical-induced ischemia and reperfusion, ischemia and reperfusion associated with organ transplantation, preservation of an ischemic and reperfused organ for organ transplantation, etc.), the invention encompasses treating a subject suspected of undergoing ischemia and reperfusion, a subject susceptible of undergoing ischemia and reperfusion, or a subject known to be undergoing ischemia and reperfusion. For example, if a subject is presented at an emergency room or other healthcare setting with symptoms of a heart attack (including, for example, chest pain, shortness of breath, etc.) the invention encompasses treating such subject by administering a fibrin beta chain derived peptide or composition thereof alone or with another peptide or composition thereof (including, for example, TB4 or an isoform, analogue, or derivative of TB4). The invention also encompasses treating a subject that is going under programmed or planned ischemia and reperfusion (including, for example, cardiac bypass surgery, angioplasty, other cardiovascular surgeries or procedures implicating ischemia and reperfusion, etc.) by administering a fibrin beta chain derived peptide or composition thereof alone or with another peptide or composition thereof (including, for example, TB4 or an isoform, analogue, or derivative of TB4). In embodiments comprising the administration of a fibrin beta chain derived peptide or composition thereof in combination with TB4 or an isoform, analogue, or derivative of TB4 or composition thereof, without being bound by theory, protection against injury associated with ischemia and reperfusion is believed to be synergistically achieved due to differing mechanisms of action of a fibrin beta chain derived peptide and TB4 or an isoform, analogue, or derivative of TB4. Again, without being bound by theory, a fibrin beta chain derived peptide or composition thereof is believed to work in part by inhibiting leukocyte (including, for example, neutrophil) migration and infiltration, which would be efficacious in terms of acute injury associated with ischemia and reperfusion, while TB4 or an isoform, analogue, or derivative of TB4 is believed to work in part by promoting myocyte survival and regeneration, which would be efficacious in terms of acute and long-term injury associated with ischemia and reperfusion.

The invention is further drawn to other pathological indications resulting from the effect of leukocyte migration and infiltration (including, for example, neutrophils) or wherein the physiological integrity of the layer of endothelial cells lining a blood vessel is impaired. A pathological indication encompassed by the invention is, for example, associated autoimmunity, including, for example, collagenoses, rheumatic diseases, inflammatory bowel diseases like Morbus Crohn or Colitis ulcerosa, psoriasis and psoriatic rheumatoid arthritis, ulcers, and post/parainfectious diseases as well as diseases caused by a graft-versus-host reaction. Without being bound by theory, it is believed that a healing effect takes place as a fibrin beta chain derived peptide or composition thereof inhibits the migration of leukocytes into the tissue and ultimately cells. Thus, leukocytes remain in the blood stream and cannot cause an autoreactive effect harmful to tissue or cells. A fibrin beta chain derived peptide or composition thereof is furthermore important for the treatment of shock, in particular in case of septic shock triggered by infection with gram-positive or gram-negative bacterial pathogens as well as viral infections and non-hemorrhagic and hemorrhagic shock caused by severe injuries or bacterial or viral infections. A fibrin beta chain derived peptide or composition thereof of the invention is furthermore encompassed for the treatment of acute inflammatory diseases and conditions including, for example, pain, acute inflammatory pelvic disease, acute inflammatory diseases or conditions of the skin (including, for example, impetigo, folliculitis, furuncle, carbuncle, sweat gland abscess, erysipelas, and cellulites), acute inflammatory demyelinating polyneuropathy (AIDP), acute inflammation of an organ or tissue (including, hepatitis, pancreatitis, gastritis, and nephritis), acute inflammatory reactions associated with lupus, and other acute inflammatory diseases and conditions. A fibrin beta chain derived peptide or composition thereof may also be used in situations that can be described with the terms "Systemic Inflammatory Response Syndrome (SIRS);" "Acute Respiratory Distress Syndrome (ARDS);" organ or multiple organ failure; and treatment or prevention of rejection reactions of organ transplantation. In particular embodiments, the invention is drawn to treating the above pathological indications in the acute phase of injury associated therewith.

In certain embodiments of the invention, a fibrin beta chain derived peptide or composition comprising the same encompasses a fibrin beta chain derived peptide in a modified or derivative form (including, for example, polyethylene glycol (PEG) modification or derivatization). WO92/16221 describes peptides that are covalently linked to long-chain polymers of PEG. The binding of a peptide to such polymers frequently results in a prolongation of the biological half-life of these peptides and delays their metabolism and excretion. A summary of these properties is described by, for example, Davis et al. (Polymeric Materials Pharmaceuticals for Biomedical Use (1980), pp. 441-451). The addition of a PEG-group exerts an increase in biological half-life in a way proportional to the molecular weight of the PEGylated peptide (up to a certain size), as a result of, for example, glomular filtration rate being inversely proportional to molecular weight (see also, for example, U.S. Pat. No. 7,273,909, which describes pegylation of polypeptides and other biomolecules; US Patent Application Publication No. 20050107297, which describes PEG-modified compounds and their use, in particular with emphasis on modified peptides activating the erythropoietin receptor; further examples describing covalent modification of peptides and proteins with PEG residues are interleukins (Knauf et al., J. Biol Chem. 1988, 263, 15064; Tsutumi et al., J. Controlled Release 1995, 33, 447), interferons (Kita et al., Drug Delivery Res. 1990, 6 157), catalase (Abuchowski et al., J. Biol. Chem. 1997, 252, 3582)).

Prolonged biological half-life is advantageous for various therapeutic uses of a fibrin beta chain derived peptide of the invention. This is particularly true in cases where the administration of a fibrin beta chain derived peptide of the invention is desired to be effective over a prolonged period for which the existing half-life may not accommodate. For such indications this may improve the subject's compliance (e.g., as self or non-self administration of a fibrin beta chain derived peptide or composition thereof of the invention once a day, for example, will be accepted and more easy to administer than continuous infusion) and efficacy. Apart from increasing the molecular mass by covalent modification, a prolongation of the persistency of polypeptides may be obtained by modifying them in such a way that degradation by proteolytic enzymes (e.g. exo- or endoproteases or peptidases) of a fibrin beta chain derived peptide of the invention is prevented.

PEG can have a molecular weight of about, for example, between 0.5 Kd and 100 Kd, this molecular weight being the minimum and maximum of a molecular weight distribution, so that individual components of the mixture may have a higher or lower molecular weight. In certain embodiments, PEG has a molecular weight of about 5 Kd to 50 Kd. In other certain embodiments, PEG has a molecular weight of about 5 Kd to 30 Kd. In further other certain embodiments, PEG has a molecular weight of about 5 Kd to 10 Kd. In even further other embodiments, PEG has a molecular weight of about 0.5 Kd, 0.6 Kd, 0.7 Kd, 0.8 Kd, 0.9 Kd, 1 Kd, 1.1 Kd, 1.2 Kd, 1.3 Kd, 1.4 Kd, 1.5 Kd, 1.6 Kd, 1.7 Kd, 1.8 Kd, 1.9 Kd, 2 Kd, 2.1 Kd, 2.2 Kd, 2.3 Kd, 2.4 Kd, 2.5 Kd, 2.6 Kd, 2.7 Kd, 2.8 Kd, 2.9 Kd, 3 Kd, 3.1 Kd, 3.2 Kd, 3.3 Kd, 3.4 Kd, 3.5 Kd, 3.6 Kd, 3.7 Kd, 3.8 Kd, 3.9 Kd, 4 Kd, 4.1 Kd, 4.2 Kd, 4.3 Kd, 4.4 Kd, 4.5 Kd, 4.6 Kd, 4.7 Kd, 4.8 Kd, 4.9 Kd, 5 Kd, 5.1 Kd, 5.2 Kd, 5.3 Kd, 5.4 Kd, 5.5 Kd, 5.6 Kd, 5.7 Kd, 5.8 Kd, 5.9 Kd, 6 Kd, 6.1 Kd, 6.2 Kd, 6.3 Kd, 6.4 Kd, 6.5 Kd, 6.6 Kd, 6.7 Kd, 6.8 Kd, 6.9 Kd, 7 Kd, 7.1 Kd, 7.2 Kd, 7.3 Kd, 7.4 Kd, 7.5 Kd, 7.6 Kd, 7.7 Kd, 7.8 Kd, 7.9 Kd, 8 Kd, 8.1 Kd, 8.2 Kd, 8.3 Kd, 8.4 Kd, 8.5 Kd, 8.6 Kd, 8.7 Kd, 8.8 Kd, 8.9 Kd, 9 Kd, 9.1 Kd, 9.2 Kd, 9.3 Kd, 9.4 Kd, 9.5 Kd, 9.6 Kd, 9.7 Kd, 9.8 Kd, 9.9 Kd, 10 Kd, 10.25 Kd, 10.5 Kd, 10.75 Kd, 11 Kd, 11.25 Kd, 11.5 Kd, 11.75 Kd, 12 Kd, 12.25 Kd, 12.5 Kd, 12.75 Kd, 13 Kd, 13.25 Kd, 13.5 Kd, 13.75 Kd, 14 Kd, 14.25 Kd, 14.5 Kd, 14.75 Kd, 15 Kd, 15.25 Kd, 15.5 Kd, 15.75 Kd, 16 Kd, 16.25 Kd, 16.5 Kd, 16.75 Kd, 17 Kd, 17.25 Kd, 17.5 Kd, 17.75 Kd, 18 Kd, 18.25 Kd, 18.5 Kd, 18.75 Kd, 19 Kd, 19.25 Kd, 19.5 Kd, 19.75 Kd, 20 Kd, 20.25 Kd, 20.5 Kd, 20.75 Kd, 21 Kd, 21.25 Kd, 21.5 Kd, 21.75 Kd, 22 Kd, 22.25 Kd, 22.5 Kd, 22.75 Kd, 23 Kd, 23.25 Kd, 23.5 Kd, 23.75 Kd, 24 Kd, 24.25 Kd, 24.5 Kd, 24.75 Kd, 25 Kd, 25.25 Kd, 25.5 Kd, 25.75 Kd, 26 Kd, 26.25 Kd, 26.5 Kd, 26.75 Kd, 27 Kd, 27.25 Kd, 27.5 Kd, 27.75 Kd, 28 Kd, 28.25 Kd, 28.5 Kd, 28.75 Kd, 29 Kd, 29.25 Kd, 29.5 Kd, 29.75 Kd, 30 Kd, 30.25 Kd, 30.5 Kd, 30.75 Kd, 31 Kd, 31.25 Kd, 31.5 Kd, 31.75 Kd, 32 Kd, 32.25 Kd, 32.5 Kd, 32.75 Kd, 33 Kd, 33.25 Kd, 33.5 Kd, 33.75 Kd, 34 Kd, 34.25 Kd, 34.5 Kd, 34.75 Kd, 35 Kd, 35.25 Kd, 35.5 Kd, 35.75 Kd, 36 Kd, 36.25 Kd, 36.5 Kd, 36.75 Kd, 37 Kd, 37.25 Kd, 37.5 Kd, 37.75 Kd, 38 Kd, 38.25 Kd, 38.5 Kd, 38.75 Kd, 39 Kd, 39.25 Kd, 39.5 Kd, 39.75 Kd, 40 Kd, 40.25 Kd, 40.5 Kd, 40.75 Kd, 41 Kd, 41.25 Kd, 41.5 Kd, 41.75 Kd, 42 Kd, 42.25 Kd, 42.5 Kd, 42.75 Kd, 43 Kd, 43.25 Kd, 43.5 Kd, 43.75 Kd, 44 Kd, 44.25 Kd, 44.5 Kd, 44.75 Kd, 45 Kd, 45.25 Kd, 45.5 Kd, 45.75 Kd, 46 Kd, 46.25 Kd, 46.5 Kd, 46.75 Kd, 47 Kd, 47.25 Kd, 47.5 Kd, 47.75 Kd, 48 Kd, 48.25 Kd, 48.5 Kd, 48.75 Kd, 49 Kd, 49.25 Kd, 49.5 Kd, 49.75 Kd, 50 Kd, 50.5 Kd, 51 Kd, 51.5 Kd, 52 Kd, 52.5 Kd, 53 Kd, 53.5 Kd, 54 Kd, 54.5 Kd, 55 Kd, 55.5 Kd, 56 Kd, 56.5 Kd, 57 Kd, 57.5 Kd, 58 Kd, 58.5 Kd, 59 Kd, 59.5 Kd, 60 Kd, 60.5 Kd, 61 Kd, 61.5 Kd, 62 Kd, 62.5 Kd, 63 Kd, 63.5 Kd, 64 Kd, 64.5 Kd, 65 Kd, 65.5 Kd, 66 Kd, 66.5 Kd, 67 Kd, 67.5 Kd, 68 Kd, 68.5 Kd, 69 Kd, 69.5 Kd, 70 Kd, 70.5 Kd, 71 Kd, 71.5 Kd, 72 Kd, 72.5 Kd, 73 Kd, 73.5 Kd, 74 Kd, 74.5 Kd, 75 Kd, 75.5 Kd, 76 Kd, 76.5 Kd, 77 Kd, 77.5 Kd, 78 Kd, 78.5 Kd, 79 Kd, 79.5 Kd, 80 Kd, 80.5 Kd, 81 Kd, 81.5 Kd, 82 Kd, 82.5 Kd, 83 Kd, 83.5 Kd, 84 Kd, 84.5 Kd, 85 Kd, 85.5 Kd, 86 Kd, 86.5 Kd, 87 Kd, 87.5 Kd, 88 Kd, 88.5 Kd, 89 Kd, 89.5 Kd, 90 Kd, 90.5 Kd, 91 Kd, 91.5 Kd, 92 Kd, 92.5 Kd, 93 Kd, 93.5 Kd, 94 Kd, 94.5 Kd, 95 Kd, 95.5 Kd, 96 Kd, 96.5 Kd, 97 Kd, 97.5 Kd, 98 Kd, 98.5 Kd, 99 Kd, 99.5 Kd, or 100 Kd.

Delivery of Proteins

In certain embodiments, the present invention relates to the delivery of an amino acid sequence of the invention (including, for example, a fibrin beta chain derived peptide, TB4 or an isoform, analogue, or derivative of TB4) conjugated to, fused with, or otherwise combined with, a peptide known as a protein transduction domain ("PTD"). In certain aspects of the invention a PTD may increase the efficacy of the delivery of an amino acid sequence of the invention, including, for example, for the treatment stroke where a PTD may further facilitate efficacy due to, for example, an increase in transport across the blood brain barrier. A PTD is a short peptide that facilitates the movement of an amino acid sequence across an intact cellular membrane or barrier, including the blood brain barrier, wherein said amino acid sequence would not penetrate the intact cellular membrane without being conjugated to, fused with, or otherwise combined with a PTD. The conjugation with, fusion to, or otherwise combination of a PTD with a heterologous molecule (including, for example, an amino acid sequence, nucleic acid sequence, or small molecule) is sufficient to cause transduction into a variety of different cells in a concentration-dependent manner. Moreover, when drawn to the delivery of amino acids, it appears to circumvent many problems associated with polypeptide, polynucleotide and drug-based delivery. Without being bound by theory, PTDs are typically cationic in nature causing PTDs to track into lipid raft endosomes and release their cargo into the cytoplasm by disruption of the endosomal vesicle. PTDs have been used for delivery of biologically active molecules, including amino acid sequences (see, for example, Viehl C. T. et al. (2005) Ann. Surg. Oncol. 12:517-525; Noguchi, H., et al. (2004) Nat. Med. 10:305-309 (2004); Fu A. L., et al. (2004) Neurosci. Lett. 368:258-262; Del Gazio Moore et al. (2004) J. Biol. Chem. 279(31):32541-32544; US Application Publication No. 20070105775). For example, it has been shown that TAT-mediated protein transduction can be achieved with large proteins such as beta-galactosidase, horseradish peroxidase, RNAase, and mitochondrial malate dehydrogenase, whereby transduction into cells is achieved by chemically cross-linking the protein of interest to an amino acid sequence of HIV-1 TAT (see, for example, Fawell, S. et al. (1994) Proc. Natl. Acad. Sci. (U.S.A.) 91(2):664-668 (1994); Del Gazio, V. et al. (2003) Mol. Genet. Metab. 80(1-2):170-180 (2003)).

Protein transduction methods encompassed by the invention include an amino acid sequence of the invention conjugated to, fused with, or otherwise combined with, a PTD. In particular embodiments a PTD of the invention includes, for example, the PTD from human transcription factor HPH-1, mouse transcription factor Mph-1, Sim-2, HIV-1 viral protein TAT, Antennapedia protein (Antp) of *Drosophila*, HSV-1 structural protein Vp22, regulator of G protein signaling R7, MTS, polyarginine, polylysine, short amphipathic peptide carriers Pep-1 or Pep-2, and other PTDs known to one of ordinary skill in the art or readily identifiable to one of ordinary skill in the art (see, for example, US Application Publication No. 20070105775). One of ordinary skill in the art could routinely identify a PTD by, for example, employing known methods in molecular biology to create a fusion protein comprising a potential PTD and, for example, green fluorescent protein (PTD-GFP) and detecting whether or not GFP was able to transduce an intact cellular membrane or barrier, which can be determined by, for example, microscopy and the detection of fluorescence. It is noted that the particular PTD is not limited by any of the foregoing and the invention encompasses any known, routinely identifiable, and after-arising PTD.

Methods of protein transduction are known in the art and are encompassed by the present invention (see, for example, Noguchi, H. et al. (2006) Acta Med. Okayama 60: 1-11; Wadia, J. S. et al. (2002) Curr. Opin. Biotechnol. 13:52-56; Viehl C. T. et al. (2005) Ann. Surg. Oncol. 12:517-525; Noguchi, H., et al. (2004) Nat. Med. 10:305-309 (2004); Fu A. L., et al. (2004) Neurosci. Lett. 368:258-262; Del Gazio Moore et al. (2004) J. Biol. Chem. 279(31):32541-32544; US Application Publication No. 2007/0105775; Gump et al. (2007) Trends in Molecular Medicine, 13(10):443-448; Tilstra, J. et al. (2007) Biochem. Soc. Trans. 35(Pt 4):811-815; WO/2006/121579; US Application Publication No. 2006/0222657). In certain embodiments, a PTD may be covalently cross-linked to an amino acid sequence of the invention or synthesized as a fusion protein with an amino acid sequence of the invention followed by administration of the covalently cross-linked amino acid sequence and the PTD or the fusion protein comprising the amino acid sequence and the PTD. In other embodiments, methods for delivering an amino acid sequence of the invention includes a non-covalent peptide-based method using an amphipathic peptide as disclosed by, for example, Morris, M. C. et al. (2001) Nat. Biotechnol. 19:1173-1176 and U.S. Pat. No. 6,841,535; and indirect polyethylenimine cationization as disclosed by, for example, Kitazoe et al. (2005) J. Biochem. 137:693-701.

As a non-limiting illustration of a method of making a PTD fusion protein, an expression system that permits the rapid cloning and expression of in-frame fusion polypeptides using an N-terminal 11 amino acid sequence corresponding to amino acids 47-57 of TAT is used (Becker-Hapak, M. et al. (2001) Methods 24(3):247-56 (2001); Schwarze, F. R. et al. (1999) Science 285:1569-72; Becker-Hapak, M. et al. (2003) Curr. Protoc. Cell Biol. Chapter 20:Unit 20.2). Using this expression system, cDNA of the amino acid sequence of interest is cloned in-frame with an N-terminal 6× His-TAT-HA encoding region in the pTAT-HA expression vector. The 6× His motif provides for the convenient purification of a fusion polypeptide using metal affinity chromatography and the HA epitope tag allows for immunological analysis of the fusion polypeptide. Although recombinant polypeptides can be expressed as soluble proteins using a microorganism (including, for example, E. coli), TAT-fusion polypeptides can often be found within inclusion bodies. In the latter case, these proteins are extracted from purified inclusion bodies in a relatively pure form by lysis in denaturant, such as, for example, 8 M urea. The denaturation aids in the solubilization of the recombinant polypeptide and assists in the unfolding of complex tertiary protein structure which has been observed to lead to an increase in the transduction efficiency over highly-folded, native proteins (Becker-Hapak, M. et al. (2001) Methods 24(3):247-56 (2001)). This latter observation is in keeping with earlier findings that supported a role for protein unfolding in the increased cellular uptake of the TAT-fusion polypeptide TAT-DHFR (Bonifaci, N. et al. (1995) Aids 9:995-1000). It is thought that the higher energy of partial or fully denatured proteins may transduce more efficiently than lower energy, correctly folded proteins, in part due to increased exposure of the TAT domain. Once inside the cells, these denatured proteins are properly folded by cellular chaperones such as, for example, HSP90 (Schneider, C. et al. (1996) Proc. Natl. Acad. Sci. (U.S.A.) 93(25):14536-14541 (1996)). Following solubilization, bacterial lysates are incubated with NiNTA resin (Qiagen), which binds to the 6x His domain in the recombinant protein. After washing, proteins are eluted from the column using increasing concentrations of imidazole. Proteins are further purified using ion exchange chromatography and finally exchanged into PBS+10% glycerol by gel filtration. It is also noted that in certain embodiments where an amino sequence of the invention (including, for example, a fibrin beta chain derived peptide, TB4 or an isoform, analogue, or derivative of TB4) is conjugated to, fused with, or otherwise combined with a PTD, that such sequences can not only be recombinantly made as described in the specification, but can also be synthetically or semi-synthetically made as described in the specification or as is known by those of ordinary skill in the art.

In certain embodiments the invention encompasses administration of an amino acid sequence of the invention conjugated to, fused with, or otherwise combined with, a PTD. In other embodiments, the invention encompasses administration of a nucleic acid sequence of the invention conjugated to, fused with, or otherwise combined with, a PTD. Both, an amino acid sequence and a nucleic acid sequence can be transduced across a cellular membrane when conjugated to, fused with, or otherwise combined with, a PTD. As such, administration of an amino acid sequence and a nucleic acid sequence is encompassed by the present invention. Routes of administration of an amino acid sequence or nucleic acid sequence of the invention include, for example, intraarterial administration, epicutaneous administration, ocular administration (e.g., eye drops), intranasal administration, intragastric administration (e.g., gastric tube), intracardiac administration, subcutaneous administration, intraosseous infusion, intrathecal administration, transmucosal administration, epidural administration, insufflation, oral administration (e.g., buccal or sublingual administration), oral ingestion, anal administration, inhalation administration (e.g., via aerosol), intraperitoneal administration, intravenous administration, transdermal administration, intradermal administration, subdermal administration, intramuscular administration, intrauterine administration, vaginal administration, administration into a body cavity, surgical administration (e.g., at the location of a tumor or internal injury), administration into the lumen or parenchyma of an organ, or other topical, enteral, mucosal, or parenteral administration, or other method, or any combination of the forgoing as would be known to one of ordinary skill in the art (see, for example, REMINGTON'S PHARMACEUTICAL SCIENCES, 18th Ed. Mack Printing Company, 1990, incorporated herein by reference).

The nucleotide sequence of the Bβ chain of fibrinogen: (SEQ ID NO:1). In bold face type appears the nucleotide sequence corresponding to amino acids (AA's) 15-65:

```
atgaaaaggatggtttcttggagcttccacaaacttaaaaccatgaaacatctattattgctactattgtg tgttttctagttaagtcccaaggtgtcaacgacaatgaggagggtttcttcagtgcccgtggtcatcgac
```

-continued

```
cccttgacaagaagagagaagaggctcccagcctgaggcctgccccaccgcccatcagtggaggtggctat cgggctcgtccagccaaagcagctgccactcaaaagaaagtagaaagaaaagcccctgatgctggaggctg tcttcacgctgacccagacctgggggtgttgtgtcctacaggatgtcagttgcaagaggctttgctacaac aggaaaggccaatcagaaatagtgttgatgagttaaataacaatgtggaagctgtttcccagacctcctct tcttcctttcagtacatgtatttgctgaaagacctgtggcaaaagaggcagaagcaagtaaaagataatga aaatgtagtcaatgagtactcctcagaactggaaaagcaccaattatatatagatgagactgtgaatagca atatcccaactaaccttcgtgtgcttcgttcaatcctggaaaacctgagaagcaaaatacaaaagttagaa tctgatgtctcagctcaaatggaatattgtcgcaccccatgcactgtcagttgcaatattcctgtggtgtc tggcaaagaatgtgaggaaattatcaggaaaggaggtgaaacatctgaaatgtatctcattcaacctgaca gttctgtcaaaccgtatagagtatactgtgacatgaatacagaaaatggaggatggacagtgattcagaac cgtcaagacggtagtgttgactttggcaggaaatgggatccatataaacagggatttggaaatgttgcaac caacacagatgggaagaattactgtggcctaccaggtgaatattggcttggaaatgataaaattagccagc ttaccaggatgggacccacagaacttttgatagaaatggaggactggaaaggagacaaagtaaaggctcac tatggaggattcactgtacagaatgaagccaacaaataccagatctcagtgaacaaatacagaggaacagc cggtaatgccctcatggatggagcatctcagctgatgggagaaaacaggaccatgaccattcacaacggca tgttcttcagcacgtatgacagagacaatgacggctggttaacatcagatcccagaaacagtgttctaaa gaagacggtggtggatggtggtataatagatgtcatgcagccaatccaaacggcagatactactggggtgg acagtacacctgggacatggcaaagcatggcacagatgatggtgtagtatggatgaattggaagggtcat ggtactcaatgaggaagatgagtatgaagatcaggcccttcttcccacagcaa
```

The nucleotide sequence corresponding to AA's 15-65 (SEQ ID NO: 2):

```
ggtcatcgacccccttgacaagaagagagaagaggctcccagcctgaggcctgccccaccgcccatcagtgg aggtggctatcgggctcgtccagccaaagcagctgccactcaaaagaaagtagaaagaaaagcccctgatg ctggaggctgt
```

The amino acid sequence corresponding to AA's 15-65 (SEQ ID NO:3):

GHRPL DKKRE EAPSL RPAPP PISGG GYRAR PAKAA ATQKK VERKA PDAGG C

A monomer amino acid sequence of (β15-66)2 (SEQ ID NO:4):

GHRPL DKKRE EAPSL RPAPP PISGG GYRAR PAKAA ATQKK VERKA PDAGG CG

A monomer amino acid sequence of (β15-44)2 (SEQ ID NO:5):

GHRPL DKKRE EAPSL RPAPP PISGG GYRCG

A monomer amino acid sequence of (β15-40)2 (SEQ ID NO:6):

GHRPL DKKRE EAPSL RPAPP PISYC G

A monomer amino acid sequence of (β15-35)2 (SEQ ID NO:7):

GHRPL DKKRE EAPSL RPAYC G

A monomer amino acid sequence of (β15-33)2 (SEQ ID NO:8):

GHRPL DKKRE EAPSL RYCG

A monomer amino acid sequence of (β15-32)2 (SEQ ID NO:9):

GHRPL DKKRE EAPSL RCG

A nucleic acid of a monomer amino acid sequence of (β15-66)2 (SEQ ID NO:10):

```
ggt cat cga ccc ctt gac aag aag aga gaa gag gct ccc agc ctg agg cct gcc cca ccg ccc atc agt gga ggt ggc tat cgg gct cgt cca gcc aaa gca gct gcc act caa aag aaa gta gaa aga aaa gcc cct gat gct gga ggc tgt ggc
```

A nucleic acid of a monomer amino acid sequence of (β15-44)2 (SEQ ID NO:11):

```
ggt cat cga ccc ctt gac aag aag aga gaa gag gct ccc agc ctg agg cct gcc cca ccg ccc atc agt gga ggt ggc tat cgg tgt ggc
```

A nucleic acid of a monomer amino acid sequence of (β15-40)2 (SEQ ID NO:12):

```
ggt cat cga ccc ctt gac aag aag aga gaa gag gct ccc agc ctg agg cct gcc cca ccg ccc atc agt tat tgt ggc
```

A nucleic acid of a monomer amino acid sequence of (β15-35)2 (SEQ ID NO:13):

```
ggt cat cga ccc ctt gac aag aag aga gaa gag gct ccc agc ctg agg cct gcc tat tgt ggc
```

A nucleic acid of a monomer amino acid sequence of (β15-33)2 (SEQ ID NO:14):

```
ggt cat cga ccc ctt gac aag aag aga gaa gag gct ccc agc ctg agg tat tgt ggc
```

A nucleic acid of a monomer amino acid sequence of (β15-32)2 (SEQ ID NO:15):

```
ggt cat cga ccc ctt gac aag aag aga gaa gag gct ccc agc ctg agg tgt ggc
```

EXAMPLE 1

The dimer (β15-66)$_2$ peptide is a more potent inhibitor of leukocyte transmigration than monomeric β15-42. We compared their anti-inflammatory effects in an in vivo peritonitis model, a well established mouse model for leukocyte migration into sites of acute inflammation. In this model, leukocyte migration from the circulation into the peritoneum was stimulated by intraperitoneal (i.p.) injection of thioglycollate, and leukocyte (neutrophil) accumulation was evaluated after 4 hours by measuring the cell number in the peritoneal lavage. The experiments presented in FIG. 2 revealed that the (β15-66)$_2$ peptide is much more potent in blocking infiltration of inflammatory leukocytes, and therefore useful for reducing inflammation and useful for myocardial reperfusion therapy.

Figure 4:
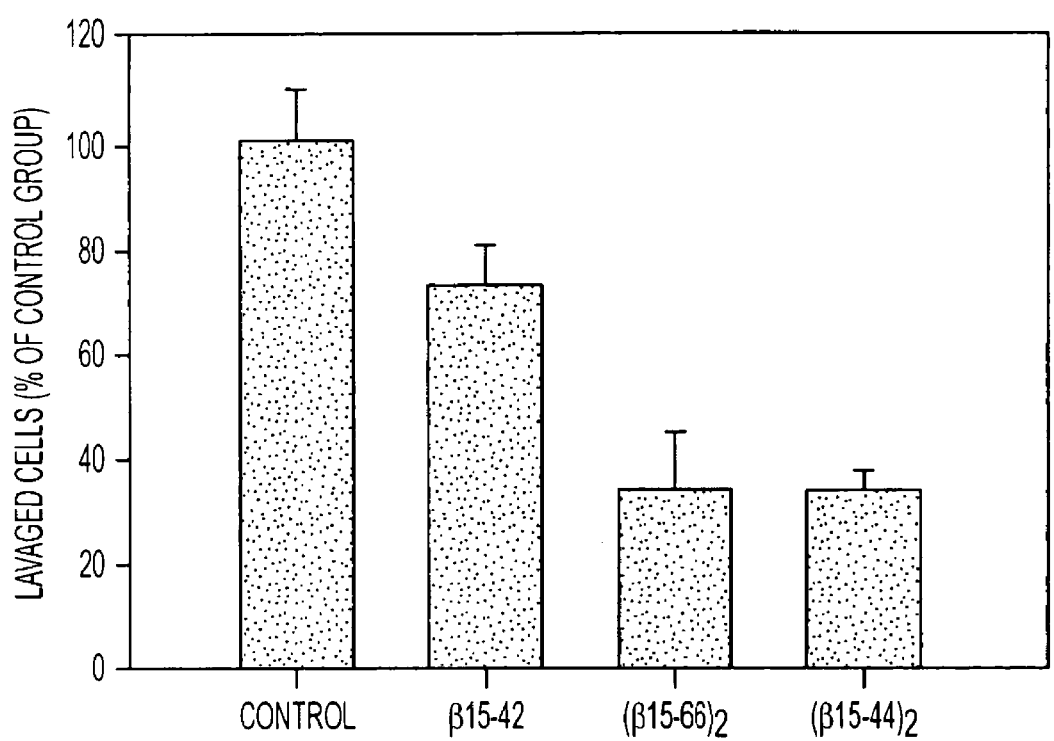
FIG. 4 graphically demonstrates ($\beta$15-66)2, ($\beta$15-44)2, and $\beta$15-42 inhibits leukocyte migration in an in vivo peritonitis model.

The (β15-66)$_2$ peptide also interacts with the endothelial cell VLDL receptor through its C-terminal portion, and it is believed that this interaction may reduce the anti-inflammatory effect of this peptide. The anti-inflammatory (and thereby cardioprotective) effect of this peptide can be further increased by deleting its VLDL receptor-binding site. We prepared the synthetic dimeric (β15-44)$_2$ peptide devoid of this site (FIG. 1d). This peptide includes two identical 30 amino acid residue polypeptides. The first 28 residues of each polypeptide correspond to the natural β15-42 sequence of human fibrin, while the last two residues, Cys43 and Gly44, were added to link two polypeptides together through a Cys43-Cys43 disulfide bond (FIG. 1d). The binding experiments revealed that the affinity of the dimeric (β15-44)$_2$ peptide to VE-cadherin is comparable to that of (β15-66)$_2$. At the same time, its inhibitory effect on leukocyte transmigration was superior over that of the (β15-66)$_2$ peptide (FIG. 4). Thus, the dimeric (β15-44)$_2$ peptide appears to be a more potent inhibitor of leukocyte transmigration and thereby useful for myocardial reperfusion therapy.

EXAMPLE 2

Synthesis of Peptide Derivatives of Fibrin Beta Chain

A fibrin beta chain derived peptide of the invention (and other peptides of the invention) is produced by, for example, recombinant means or synthetically. Recombinant production of a fibrin beta chain derived peptide is done using standard techniques known by one of ordinary skill in the art. Such methods include, for example, producing a coding nucleic acid sequences for a fibrin beta chain derived peptide of the invention, which can be done by polymerase chain reaction (PCR) based methods using as a template the full-length cDNA encoding the human fibrinogen Bbeta-chain (see, for example, GeneBank Accession No. NM_005141). Following production of the desired nucleic acid sequence, the sequence is inserted into an expression plasmid (including, for example, *Escherichia coli* pCAL-n expression plasmid), which is then transfected in a microorganism; then selection of clones containing a plasmid containing the desired sequence using selection markers (including, for example, an antibiotic resistance selection marker or a luminescent selection marker) is performed; followed by mass producing clones containing a plasmid containing the desired sequence; and purifying peptides from the desired clones (see, for example, methods described Gorlatov et al. Biochemistry (2002) 41, 4107-4116; U.S. Pat. No. 4,980,456). It is noted that the non-naturally occurring peptides of the invention (including, for example, (β15-35)2, (β15-40)2, (β15-44)2, and ((15-66)2) can be made using the above method. Alternatively peptides of the invention can be made by synthetic means or semi-synthetic means (e.g., a combination of recombinant production and synthetic means).

Synthetic production of a fibrin beta chain derived peptide of the invention (and other peptides of the invention) is done by, for example, applying a fluorenylmethyloxycarbonyl (FMOC)-protective group strategy according to Carpino L. A. and Han. G Y, J. (Amer. Chem. Soc. 1981; 37; 3404-3409) or a tert-butoxycarbonyl(t-Boc)-protective group strategy. Peptides are synthesized, for example, by means of a solid-phase peptide synthesis according to Merrifield R. B. (J. Amer. Chem. Soc. 1963; 85, 2149-2154), using a multiple peptide synthesizer. Crude peptides are then purified.

An exemplary method for the synthetic production of a fibrin beta chain derived peptide of the invention (and other peptides of the invention) is described in the following passage. 100 mg Tentagel-S-RAM (Rapp-Polymere) at a load of 0.24 mmol/g is transferred to a commercially available peptide synthesis device (PSMM(Shimadzu)), wherein the peptide sequence is constructed step-by-step according to the carbodiimide/HOBt method. The FMOC-amino acid derivatives are pre-activated by adding a 5-fold equimolar excess of di-isopropy-carbodiimide (DIC), di-isopropy-ethylamine (DIPEA) and hydroxybenzotriazole (HOBt), and following their transfer into the reaction vessel, mixed with the resin support for 30 minutes. Washing steps are carried out by, for example, additions of DMF and thorough mixing for 1 minute. Cleavage steps are carried out by, for example, the addition of piperidine in DMF and thorough mixing for 4 minutes. Removal of the individual reaction and wash solutions is effected by forcing the solutions through the bottom frit of the reaction vessel. The amino acid derivatives FMOC-Ala, FMOC-Arg(Pbf), FMOC-Asp, FMOC-Gly, FMOC-His (Trt), FMOC-Ile, FMOC-Leu, FMOC-Lys(BOC), FMOC-Pro, FMOC-Ser(tBu) and FMOC-Tyr(tBu) (Orpegen) are employed. When synthesis is completed the peptide resin is dried. The peptide amide is subsequently cleaved off by treatment with trifluoracetic acid/TIS/EDT/water (95:2:2:1 vol) for 2 hours at room temperature. By way of filtration, concentration of the solution and precipitation by the addition of ice-cold diethyl ether, the crude product is obtained as a solid. The peptide is then purified by RP-HPLC in 0.1% TFA with a gradient of 5 on 60% acetonitrile in 40 minutes at a flow rate of 12 ml/min and evaluation of the elutant by means of a UV detector at 215 nm. The purity of the individual fractions is determined by analytical RP-HPLC and mass spectrometry.

Dimerization is carried out by, for example, taking the monomer of a fibrin beta chain derived peptide of the invention (and other peptides of the invention) and forming disulfide bonds between the monomers. For example, a monomer comprising β15-66 (which contains a non-naturally occurring Gly at position 66) is purified in the presence of 1 mM DTT. The monomer is next dialyzed extensively in 20 mM Tris buffer, pH 8.0, containing 150 mM NaCl and 0.02% NaN3, to form the dimer (β15-66)2. Other means of peptide dimerization are known to those of ordinary skill in the art and also encompassed by the present invention.

EXAMPLE 3

Peptide Derivatives of Fibrin Beta Chain Bind VE-cadherin

To test binding activities of fibrin beta chain derived peptides of the invention to VE-caherin, surface plasmon resonance (SPR) methods are, for example, used. SPR experiments are performed using, for example, a BIAcore 3000 biosensor (BIAcore AB, Uppsala, Sweden), which can be used to measure the association/dissociation of peptides or proteins in real-time (see, for example, Karlsson, R., and Falt, A. J. Immunol. Methods (1997) 200, 121-133; Hall, D. Anal. Biochem. (2001) 288, 109-125; see also Gorlatov et al. Biochemistry (2002) 41, 4107-4116 for other VE-cadherin binding assays including, for example, SPR IAsys Analysis based assays and ELISA based assays). An exemplary method is described in the following passage. VE-cadherin fragment is covalently coupled via epsilon-amino groups to the activated surface of a CM5 biosensor chip by the procedure described by, for example, Karlsson, R., and Falt, A. (J. Immunol. Methods (1997) 200, 121-133; see also Gorlatov et al. Biochemistry (2002) 41, 4107-4116). Briefly, the carboxyl groups on the sensor surface were activated with an injection of a solution containing, for example, 0.2 M N-ethyl-N-(3-diethylamino-propyl) carbodiimide and 0.05 M N-hydroxysuccinimide. VE-cadherin to be coupled is prepared in 10 mM sodium-acetate buffer, pH 4.0, containing 1 mM CaCl2, and injected onto the activated CM5 surface at 5 mL/min followed by incubation for 7 min after which the surface was deactivated by passing 1 M ethanolamine. Activation time, ligand concentration, and contact time are adjusted to achieve a coupling density of 5-6 ng/mm2. Binding experiments are performed, for example, in 10 mM Hepes buffer, pH 7.4, containing 200 mM NaCl, 1 mM CaCl2, 0.02% NaN3, and 0.05% n-octyl beta-D-glucopyranoside (binding buffer). Samples comprising, for example, fibrin beta chain derived peptides β15-42, β15-64, and (β15-66)2, at different concentrations are injected in duplicate in at least three separate experiments and the association/dissociation between the immobilized and the added peptides is monitored as the change in the SPR response. To regenerate the chip, complete dissociation of the complex was achieved by adding, for example, 20 mM Tris buffer, pH 7.5, containing 0.5 M urea, 0.5 M NaCl, and 0.5% Triton X-100, for 1 min following reequilibration with binding buffer. Experimental data are analyzed using, for example, BIAevaluation 3.0 software supplied with the instrument. Briefly, kinetic constants, kass and kdis, are estimated by global analysis of the association/dissociation curves to the 1:1 Langmurian interaction model (Morton, T. A., and Myszka, D. G. Methods Enzymol. (1998) 295, 268-294). The dissociation equilibrium constant (Kd) is calculated as Kd=kdiss/kass. It is also noted that other methods known to one of ordinary skill in the art can be used to determine binding activities of fibrin beta chain derived peptides of the invention to VE-caherin including, for example, ELISA-based methods (see, for example, Gorlatov et al. Biochemistry (2002) 41, 4107-4116).

Figure 3:
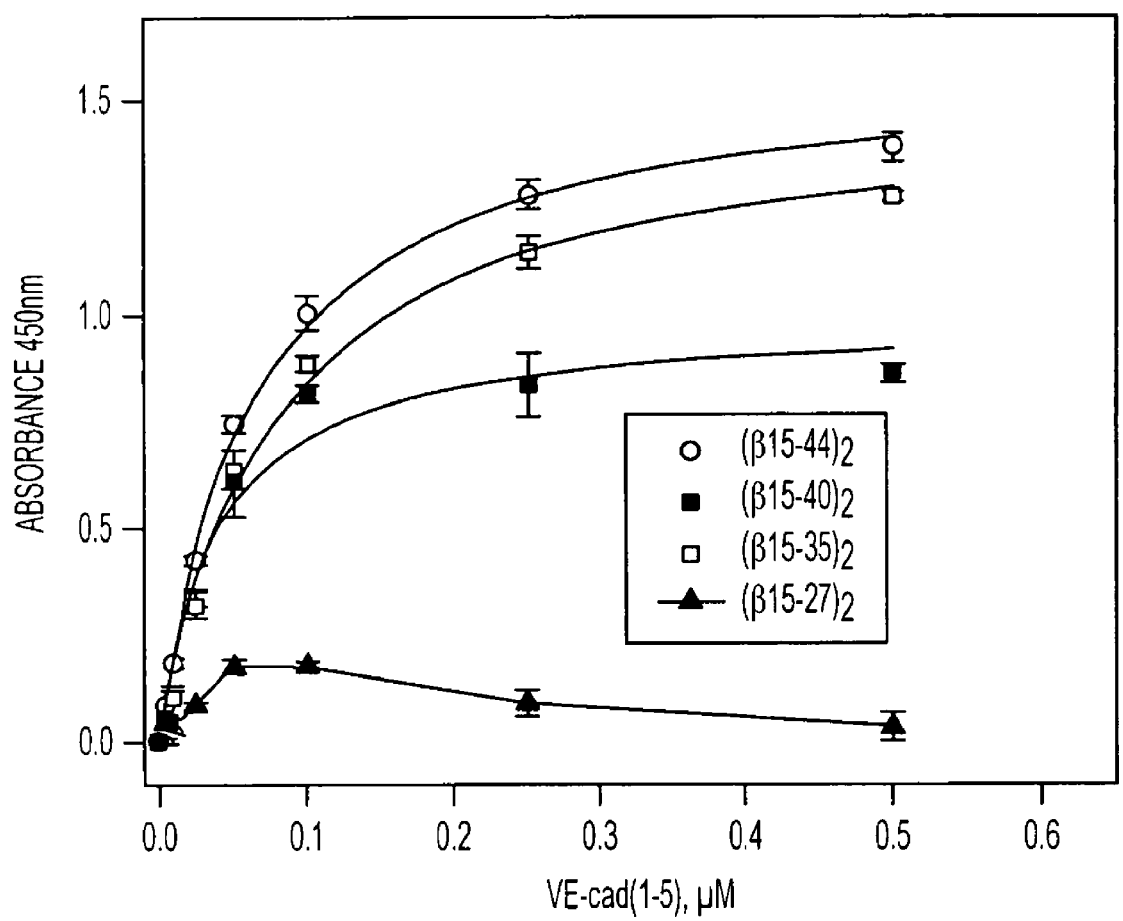
FIG. 3 graphically demonstrates binding of ($\beta$15-44)2, ($\beta$15-40)2, and ($\beta$15-35)2 to VE-cadherin.

Binding experiments using (β15-66)2, added at increasing concentrations (up to 200 nM), exhibited a dose-dependent binding to immobilized VE-cadherin fragment with a Kd=70 nM (FIG. 2, inset). At the same time, monomeric β15-64 and β15-42 both exhibited very little binding when added at 400 nM (FIG. 2); their binding was observed only at much higher concentrations. These experiments indicate that the dimeric (β15-66)2 peptide has surprisingly much higher affinity to VE-cadherin than its shorter monomeric variants. The Kd for (β15-66)2 was found to be 70 nM whereas the Kd for β15-42 was found to be 252 µM, which provided the unexpected result of an increased affinity by 3,600 fold. Additionally, experiments are conducted using fibrin beta chain derived peptides of the invention (including, for example, (β15-44)2, (β15-40)2, and (β15-35)2) and demonstrate an even higher affinity to VE-caherin (FIG. 3). In particular, (β15-35)2 demonstrated an unexpectedly higher degree of affinity to VE-cadherin when compared to both (β15-44)2 and (β15-40)2.

EXAMPLE 4

Peptide Derivatives of Fibrin Beta Chain and Compositions Comprising the Same Inhibit Inflammation in vivo Leukocyte (e.g., neutrophil) infiltration is a hallmark of injury associated with ischemia and reperfusion, as well as a number of other inflammatory conditions. Therefore, peptides of the invention are tested to determine the ability to decrease leukocyte infiltration in vivo. The ability to inhibit leukocyte infiltration was tested in an in vivo model of peritonitis, which is a well established mouse model for leukocyte infiltration and migration into sites of inflammation. The protocol for this animal model is described as below. Experiments were performed consistent with accepted practice (see, for example, Bosse et al. 1994. Eur. J. Immunol. 24: 3019; Borges et al. 1997. Blood 90: 1934; US Patent Application Publication No. 20030105020). To induce peritonitis, thioglycollate was administered intraperitoneally (i.p.) to mice. For inhibition studies, mice were injected intravenously (i.v.) with either β15-42, (β15-44)2, or (β15-66)2 prior to i.p. injection of thioglycollate (FIG. 4). Control mice were treated with the same volume of PBS. All reagents are kept endotoxin-free. At 4 h after injection of thioglycollate, mice were sacrificed and the peritoneal lavage was generated by, for example, injecting 10 ml PBS, massaging the peritoneal wall, and removing the fluid. Following the peritoneal lavage, leukocytes were quantified (e.g., neutrophil quantification determined using a hemocytometer). When mice were injected i.v. with either β15-42 or (β15-66)2 prior to i.p. injection of thioglycollate, the number of leukocytes accumulating in the peritoneum was significantly lower than in control mice injected with PBS. Additionally, when (β15-44)2 is compared to β15-44 there is also a decrease in the number of leukocytes. This demonstrates that all three peptides inhibited leukocyte infiltration and migration into sites of inflammation, however, the extent of inhibition by (β15-66)2 and (β15-44)2 was unexpectedly almost twice as much as that of β15-42.

Figure 5:
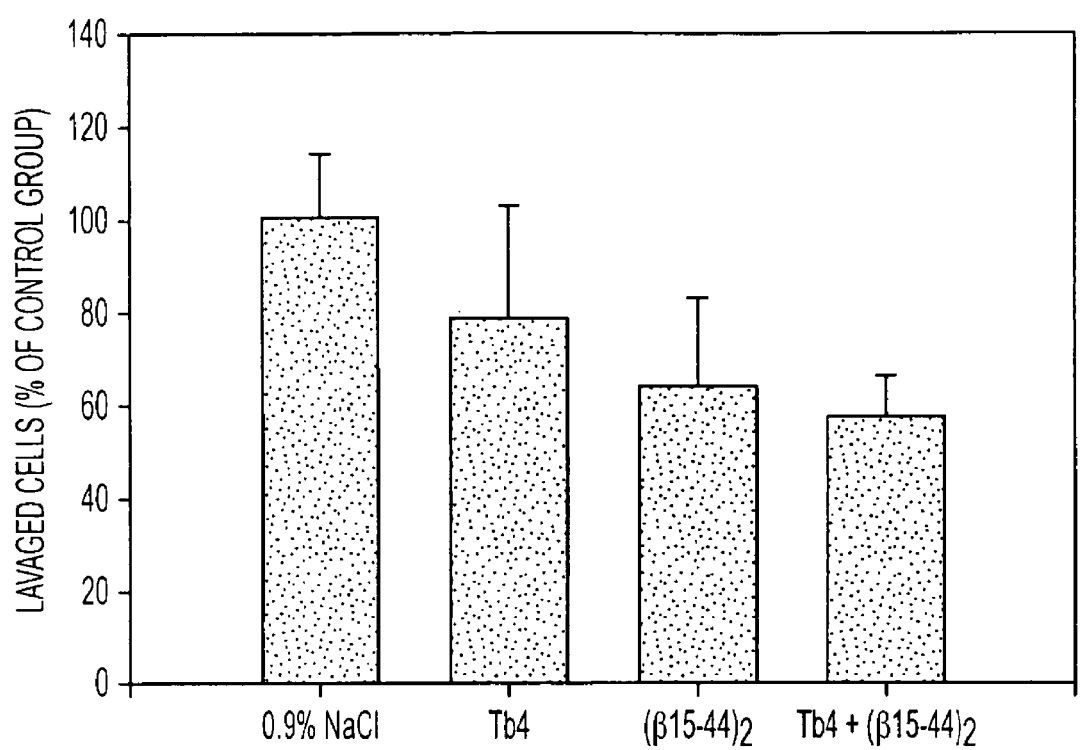
FIG. 5 graphically demonstrates ($\beta$15-44)2, TB4, and a combination of ($\beta$15-44)2 plus TB4 inhibits leukocyte migration in an in vivo peritonitis model.

Experiments are also conducted using other fibrin beta chain derived peptides of the invention (including, for example, (β15-35)2 and (β15-40)2), which demonstrate the ability to even further inhibit leukocyte infiltration and migration when compared to β15-42. Experiments are also conducted using a combination of a fibrin beta chain derived peptide and TB4, which demonstrate an even further inhibition of leukocyte infiltration and migration when compared to using a fibrin beta chain derived peptide of the invention by itself (FIG. 5). The result of the combination of a fibrin beta chain derived peptide and TB4 demonstrate that the combination can be used to decrease inflammation and therefore decrease injury or tissue damage associated with inflammation.

EXAMPLE 5

Peptide Derivatives of Fibrin Beta Chain and Compositions Comprising the Same Inhibit Injury Following in vivo Ischemia and Reperfusion To confirm the ability of (β15-66)2, (β15-44)2, (β15-40)2, (β15-35)2, and β15-42 to protect (with the former peptides showing increased protection over β15-42) against injury following ischemia and reperfusion an animal model of myocardial infarction (MI) is employed. The effect of the β15-42, (β15-66)2, (β15-44)2, (β15-40)2, and (β15-35)2 (and other fibrin beta chain derived peptides of the invention) on the protection and infiltration and migration of leukocytes into the ischemic myocardium is determined by, for example, using a coronary artery ligation mouse model of MI. To determine the efficacy of these peptides to protect against injury and inhibit leukocyte infiltration and migration into the myocardium following ischemia a fibrin beta chain derived peptide is administered (for example, at a dose of about 16 nanomoles, which can be adjusted accordingly to determine efficacy) i.v. into 8-12 week-old C57BL6 mice (20 to 25 g), for example, prior to left anterior descending (LAD) coronary artery ligation, upon reperfusion, or after reperfusion. Mice injected with PBS are used as controls. As a starting point for the dosage of these peptides, the dosage is chosen based on results in which a significant inhibition of leukocyte infiltration and migration into the peritoneum are demonstrated using the above-recited peritonitis model of inflammation. Administration can be adjusted based on, for example, pharmacodynamic and pharmacokinetic properties.

The study may comprise at least 7 different groups: sham-operated control (group #1), MI mice with no treatment (group #2), and MI mice treated with β15-42 (group #3), (β15-66)2 (group #4), (β15-44)2 (group #5), (β15-40)2 (group #6), and (β15-35)2 (group #7). To ensure objectivity, these experiments are conducted in a double-blind and placebo-controlled manner. Thus, β15-42, (β15-66)2, (β15-44)2, (β15-40)2, (β15-35)2, and PBS are assigned randomly to a reference number, which is blinded to the personnel involved in conducting the surgery and performing post-surgery analysis. Analysis of induced MI and protection thereof are conducted using, for example, end point measures comprising hemodynamic parameters (including, for example, developed pressure, end diastolic pressure, dP/dtmax/left ventricular pressure (see, for example, Wada et al., European Journal of Pharmacology (2005) 507(1-3),145-151)), troponin, creatine kinase, infarct size, and histological analysis using, for example, hematoxylin and eosin (H&E) staining to determine leukocyte infiltration and general cellular architecture. In preparation for analysis, mice are euthanized and perfused, followed by excision of the heart for end point measurements. For microscopy analysis, a total of, for example, 6 sections per heart are used. The ischemic zone of the hearts is identified by staining with a 1% solution of triphenyltetrazolium chloride (TTC) in PBS. Leukocyte infiltration into the ischemic myocardium is determined by H&E staining and cardiomyocyte apoptosis is determined by TdT-mediated dUTP Nick-End Labeling (TUNEL) staining. To further determine the specific sub-types of the infiltrated leukocytes, immunohistochemistry is preformed on different groups of MI hearts using antibodies specific for neutrophils and macrophages.

Following the above methods, and others known by one of ordinary skill in the art, the peptides (β15-66)2, (β15-44)2, (β15-40)2, and (β15-35)2 demonstrate increased efficacy when compared to β15-42.

Example 6

Peptide Derivatives of Fibrin Beta Chain and TB4 or an Isoform, Analogue, or Derivative of TB4, and Compositions Comprising the Same Synergistically Inhibit Injury Following in vivo Ischemia and Reperfusion To confirm the ability of (β15-66)2, (β15-44)2, (β15-40)2, and (β15-35)2 in combination with TB4 or an isoform, analogue, or derivative of TB4 to protect against injury following ischemia and reperfusion an animal model of myocardial infarction (MI) is employed. The effect of the (β15-66)2, (β15-44)2, (β15-40)2, or (β15-35)2 (and other fibrin beta chain derived peptides of the invention) in combination of TB4 or an isoform, analogue, or derivative of TB4 on the protection, and infiltration and migration of leukocytes into the ischemic myocardium is determined by, for example, using a coronary artery ligation mouse model of MI. To determine the efficacy of these peptides to protect against injury and inhibit leukocyte infiltration and migration into the myocardium following ischemia, a fibrin beta chain derived peptide is administered (for example, at a dose of about 16 nanomoles, which can be adjusted accordingly to determine efficacy) and TB4 or an isoform, analogue, or derivative of TB4 is administered (for example, at a dose of about 31 nanomoles, which can be adjusted accordingly to determine efficacy) i.v. into 8-12 week-old C57BL6 mice (20 to 25 g) for example, prior to left anterior descending (LAD) coronary artery ligation, upon reperfusion, or after reperfusion. Mice injected with PBS are used as controls. As a starting point for the dosage of a fibrin beta chain derived peptide and TB4 or an isoform, analogue, or derivative of TB4, the dosage is chosen based on results in which a significant inhibition of leukocyte infiltration and migration into the peritoneum are demonstrated using the above-recited peritonitis model of inflammation. Administration can be adjusted based on, for example, pharmacodynamic and pharmacokinetic properties.

The study may comprise at least 10 different groups: sham-operated control (group #1), MI mice with no treatment (group #2), and MI mice treated with, (β15-66)2 (group #3), (β15-44)2 (group #4), (β15-40)2 (group #5), (β15-35)2 (group #6), (β15-66)2 plus TB4 (group #7), (β15-44)2 plus TB4 (group #8), (β15-40)2 plus TB4 (group #9), and (β15-35)2 plus TB4 (group #10). To ensure objectivity, these experiments are conducted in a double-blind and placebo-controlled manner. Thus, (β15-66)2, (β15-44)2, (β15-40)2, (β15-35)2, (β15-66)2 plus TB4, (β15-44)2 plus TB4, (β15-40)2 plus TB4, (β15-35)2 plus TB4, and PBS are assigned randomly to a reference number, which is blinded to the personnel involved in conducting the surgery and performing post-surgery analysis. Analysis of induced MI are conducted using, for example, end point measures comprising hemodynamic parameters (including, for example, developed pressure, end diastolic pressure, dP/dtmax/left ventricular pressure (see, for example, Wada et al., European Journal of Pharmacology (2005) 507(1-3),145-151)), troponin, creatine kinase, infarct size, and histological analysis using, for example, hematoxylin and eosin (H&E) staining to determine leukocyte infiltration and general cellular architecture. In preparation for analysis, mice are euthanized and perfused, followed by excision of the heart for end point measurements. For microscopy analysis, a total of, for example, 6 sections per heart are used. The ischemic zone of the hearts is identified by staining with a 1% solution of triphenyltetrazolium chloride (TTC) in PBS. Leukocyte infiltration into the ischemic myocardium is determined by H&E staining and cardiomyocyte apoptosis is determined by TdT-mediated dUTP Nick-End Labeling (TUNEL) staining. To further determine the specific sub-types of the infiltrated leukocytes, immunohistochemistry is preformed on different groups of MI hearts using antibodies specific for neutrophils and macrophages. Scare tissue can also be quantified and used as an indicator of tissue protection. Methods of quantifying scare tissue are known to one of ordinary skill in the art (see, for example, Bonnefont-Rousselot et al., Redox Report, Volume 7, Number 3, June 2002, pp. 145-151(7)).

It is noted that for in vivo ischemia and reperfusion experiments (as well as other experiments where appropriate), the time course is to be determined while considering, inter alia, what end points are being tested. For example, for long-term survival, quantification of scare tissue, or myocyte regeneration, animals may not be scarified until weeks or even months following reperfusion whereas a determination of neutrophil infiltration may be determined with animals being sacrificed only hours following reperfusion. In the case of myocyte regeneration, the above laid out protocol is followed with the additional step of administering TB4 or an isoform, analogue, or derivative of TB4 three times a week following reperfusion to maintain its adequate level in the circulation. Animals are sacrificed 14 and 28 days following reperfusion. Regeneration of the myocardium will be evaluated histologically using 6 sections per heart, as described above. Additionally, mice are evaluated by 2D-echocardiography. Gross morphology of the heart, including their LV end-diastolic dimension, LV end-systolic dimension, and fractional shortening are measured by 2D-echocardiography using the M-mode.

Following the above methods, and others known by one of ordinary skill in the art, the combination of (β15-66)2, (β15-44)2, (β15-40)2, or (β15-35)2 with TB4 or an isoform, analogue, or derivative of TB4 demonstrates an increased, additive or synergistic effect on efficacy when compared to a fibrin beta chain derived peptide alone.

EXAMPLE 7

Figure 6:
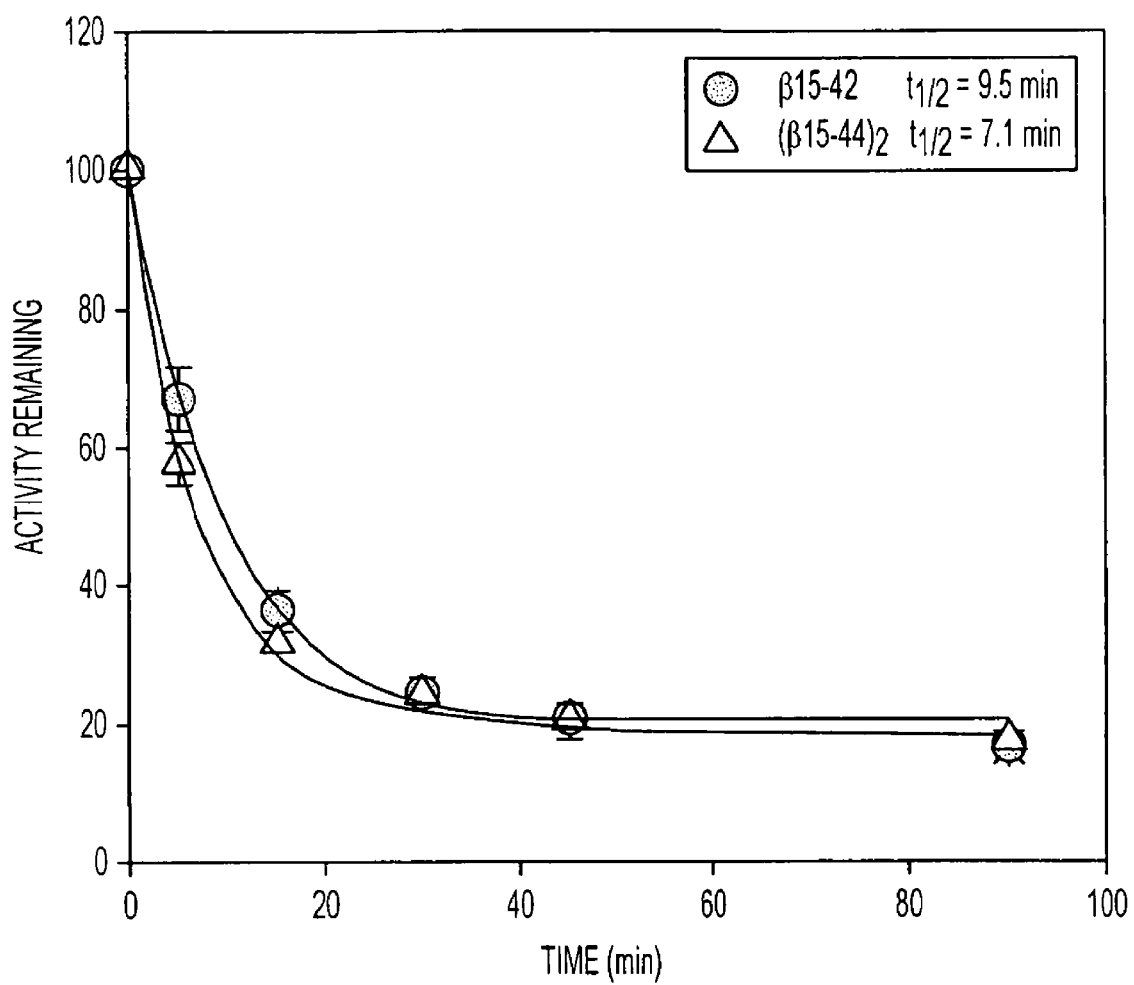
FIG. 6 graphically demonstrates clearance of $\beta$15-42 and ($\beta$15-44)2 in vivo.

Peptide Derivatives of Fibrin Beta Chain and Compositions Comprising the Same for the Treatment of Acute Inflammation A fibrin beta chain derived peptide of the invention has been shown to inhibit inflammation (see, for example, peritonitis data described herein). In addition, a fibrin beta chain derived peptide of the invention has a half-life that is particularly suited for treating acute inflammation (FIG. 6). Half-life was measured using radiolabeled peptides. Briefly, (β15-44)2 and β15-42 were labeled with 125I using iodogen tubes with removal of free iodine by desalting over a NAP-5 (GE Healthcare) column in PBS, followed by injection into 9-week old C57BL/6 male mice. Each labeled peptide was mixed with cold peptide to a final concentration of 0.38 mg/ml for (β15-44)2 and 0.19 mg/ml for β15-42. Mice tail veins were injected with 200 μl of 60 μM 125I-labeled (β15-44)2 which corresponded to $13 \times 10^6$ cpm and 200 μl of 60 μM 125I-labeled β15-42 which corresponded to $3.6 \times 10^6$ cpm. At various times following tail vein injection, blood was removed from the orbital sinus. Blood was centrifuged at 7000 rpm for 4 min at 4° C. Samples (20 μl serum) were counted on a Wallac Wizard 1470 gamma-counter. Based on the ability to inhibit inflammation and the half-life profile of fibrin beta chain derived peptides of the invention, these peptides are particularly well-suited for the treatment of acute inflammation.

The invention claimed is:

1. An isolated peptide comprising an amino acid sequence of a fibrin beta chain fragment of a Bbeta chain of fibrinogen wherein said peptide comprises an amino acid sequence selected from the group consisting of SEQ ID NO: 5, SEQ ID NO: 6, SEQ ID NO: 7, SEQ ID NO: 8, and SEQ ID NO: 9.

2. The peptide of claim 1, wherein said peptide comprises wild-type β15-42.

3. The peptide of claim 1, wherein said peptide is in monomeric or dimeric form.

4. The peptide of claim 3, wherein said peptide is in dimeric form.

5. The peptide of claim 4, wherein said dimer comprises two identical peptides, each of said peptides being linked at C-terminal ends thereof, and said dimer having fewer than 104 amino acid residues in total.

6. The peptide of claim 4, wherein said dimer is disulfide linked at a Cys residue in said peptide.

7. The peptide of claim 1, wherein said peptide is PEGylated.

8. The peptide of claim 1, wherein said peptide is conjugated to, fused with, or combined with a protein transduction domain (PTD).

9. A composition comprising the peptide of claim 1.

10. A method of treating ischemia and reperfusion in a subject in need thereof, comprising administering to the subject a peptide comprising an amino acid sequence selected from the group consisting of SEQ ID NO: 5, SEQ ID NO: 6, SEQ ID NO: 7, SEQ ID NO: 8, and SEQ ID NO: 9.

11. The method of claim 10, wherein said peptide is in monomeric or dimeric form.

12. The method of claim 11, wherein said peptide is in dimeric form.

13. The method of claim 12, wherein said dimer comprises two identical peptides, each of said peptides being linked at C-terminal ends thereof, and said dimer having fewer than 104 amino acid residues in total.

14. The method of claim 12, wherein said dimer is disulfide linked at a Cys residue in said peptide.

15. The method of claim 10, wherein said peptide is PEGylated.

16. The method of claim 10, wherein said peptide is conjugated to, fused with, or combined with a protein transduction domain (PTD).

17. The method of claim 10, wherein said ischemia and reperfusion is ischemia and reperfusion in the myocardium.

* * * * *

UNITED STATES PATENT AND TRADEMARK OFFICE
CERTIFICATE OF CORRECTION

PATENT NO. : 8,722,623 B2
APPLICATION NO. : 12/678122
DATED : May 13, 2014
INVENTOR(S) : Medved et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 712 days.

Signed and Sealed this

Twenty-ninth Day of September, 2015

Michelle K. Lee
*Director of the United States Patent and Trademark Office*

UNITED STATES PATENT AND TRADEMARK OFFICE
CERTIFICATE OF CORRECTION

| | |
|---|---|
| PATENT NO. | : 8,722,623 B2 |
| APPLICATION NO. | : 12/678122 |
| DATED | : May 13, 2014 |
| INVENTOR(S) | : Leonid Medved, Li Zhang and Sergiy Yakovlev |

Page 1 of 1

It is certified that error appears in the above-identified patent and that said Letters Patent is hereby corrected as shown below:

Specification

Insert the following starting at Column 1, line 13:

-- STATEMENT OF GOVERNMENT SUPPORT

This invention was made with government support under Grant Number HL056051 awarded by the National Institutes of Health. The government has certain rights in the invention. --

Signed and Sealed this
Sixteenth Day of February, 2016

Michelle K. Lee
*Director of the United States Patent and Trademark Office*